US008658648B2

(12) United States Patent
Peyton et al.

(10) Patent No.: US 8,658,648 B2
(45) Date of Patent: Feb. 25, 2014

(54) MODIFIED CHLOROQUINES WITH SINGLE RING MOIETY OR FUSED RING MOIETY

(75) Inventors: David H. Peyton, Portland, OR (US); Steven J. Burgess, Tualatin, OR (US); Katherine M. Liebman, Portland, OR (US); Bornface Gunsaru, Portland, OR (US)

(73) Assignees: DesignMedix, Inc., Portland, OR (US); Portland State University, Portland, OR (US)

( * ) Notice: Subject to any disclaimer, the term of this patent is extended or adjusted under 35 U.S.C. 154(b) by 195 days.

(21) Appl. No.: 13/132,742

(22) PCT Filed: Dec. 4, 2009

(86) PCT No.: PCT/US2009/066879
§ 371 (c)(1),
(2), (4) Date: Jun. 3, 2011

(87) PCT Pub. No.: WO2010/065932
PCT Pub. Date: Jun. 10, 2010

(65) Prior Publication Data
US 2011/0251210 A1  Oct. 13, 2011

Related U.S. Application Data

(60) Provisional application No. 61/120,313, filed on Dec. 5, 2008.

(51) Int. Cl.
*A61K 31/4706* (2006.01)
*A61K 31/496* (2006.01)
*C07D 215/42* (2006.01)
*A61K 31/506* (2006.01)

(52) U.S. Cl.
USPC .. 514/253.06; 544/363; 544/295; 514/252.18

(58) Field of Classification Search
None
See application file for complete search history.

(56) References Cited

U.S. PATENT DOCUMENTS

| 4,146,625 | A  | 3/1979 | Lee |
| 4,382,892 | A  | 5/1983 | Hayakawa et al. |
| 4,898,945 | A  | 2/1990 | Williams |
| 6,964,966 | B2 | 11/2005 | De Souza et al. |
| 7,404,962 | B1 | 7/2008 | Pinto et al. |
| 2006/0074105 | A1 | 4/2006 | Ware, Jr. et al. |
| 2008/0188462 | A1 | 8/2008 | Peyton et al. |

FOREIGN PATENT DOCUMENTS

| GB | 1021950 | * 11/1964 |
| WO | WO200059510 | 10/2000 |
| WO | WO2010065925 | 6/2010 |
| WO | WO2010065932 | 6/2010 |
| WO | WO2011034971 | 3/2011 |

OTHER PUBLICATIONS

CA Registry No. 950147-22-5, entered into the Registry File on Oct. 10, 2007, supplied by Enamine.*
CA Registry No. 471293-94-4, entered into the Registry File on Nov. 7, 2002, supplied by Chembridge Corporation.*
CA Registry No. 298203-51-7, entered into the Registry File on Oct. 23, 2000, supplied by Scientific Exchange, Inc.*
Vippagunta et al Advanced Drug Delivery Reviews, vol. 48, pp. 3-26 (2001).*
ISR/WO from PCT/US2010/048996, dated Oct. 22, 2010.
ISR/WO from PCT/US2009/066871, dated Jan. 26, 2010.
ISR/WO from PCT/US2009/066879, dated Feb. 23, 2010.
Extended European Search Report, EP App. No. 09831248.1, dated Sep. 17, 2012.
Mahajan, A. et al., "Synthesis of new 7-chloroquinolinyl thioureas and their biological investigation as potential antimalarial and anticancer agents," Bioorganic & Medicinal Chemistry Letters 17 (2007) 5683-5685.

* cited by examiner

*Primary Examiner* — Emily Bernhardt
(74) *Attorney, Agent, or Firm* — Hema Vakharia-Rao; Nixon Peabody LLP

(57) ABSTRACT

The disclosure provides modified chloroquine compounds having single ring or fused ring moieties. Also provided are pharmaceutical compositions comprising such compounds, methods of using such compounds to inhibit or treat diseases or conditions caused by chloroquine-resistant ($CQ^R$) and chloroquine-sensitive ($Cq^S$) malaria parasites and other CQ-susceptible microorganisms, and processes and intermediates useful for preparing such compounds.

6 Claims, 2 Drawing Sheets

MODIFIED CHLOROQUINES WITH SINGLE RING MOIETY OR FUSED RING MOIETY

CROSS-REFERENCE TO RELATED APPLICATIONS

This application is a U.S. National Stage entry under 35 U.S.C. §371 of International Application PCT/US09/66879, filed Dec. 4, 2009, which designated the U.S. and was published under PCT Article 21(2) in English on Jun. 10, 2010. This application also includes a claim of priority under 35 U.S.C. §119(e) to U.S. Provisional Patent Application No. 61/120,313, filed Dec. 5, 2008, the entire contents of which are incorporated herein by reference.

STATEMENT REGARDING U.S. SPONSORED RESEARCH OR DEVELOPMENT

This invention was made in part with U.S. government support under Grant Nos. R41AI07923 and R21AI067837 as awarded by the U.S. National Institutes of Health. The U.S. government has certain rights in the invention.

FIELD OF THE INVENTION

The invention disclosed herein generally relates to compositions comprising modified chloroquine compounds having single ring or fused ring moieties and methods of using the same for therapeutic and research applications.

BACKGROUND

Malaria is a disease caused by various species of hemosporidian blood parasites of the genus *Plasmodium* (including *P. falciparum, P. vivax, P. ovule,* and *P. malariae*). The human disease process begins with the bite of an infected female Anopheline mosquito. *Plasmodium* sporozoites released from the salivary glands of the mosquito enter the bloodstream and quickly (within about 30 minutes) invade liver cells (hepatocytes). The liver-stage parasites differentiate and undergo asexual multiplication resulting in tens of thousands of merozoites which burst from the hepatoctye. Merozoites then invade red blood cells (erythrocytes) where they undergo an additional round of multiplication. The clinical signs of malaria, fever and chills, are associated with the synchronous rupture of infected erythrocytes.

Malaria is a worldwide public health problem. Up to 3 million people die of malaria each year, and the total number of people infected with malaria worldwide approaches half a billion. The impact of this disease, in terms of suffering and economics, is enormous. In the past, the inexpensive and orally administered antimalarial drug, chloroquine (CQ), was considered the "gold standard" treatment.

During its blood stage, the malaria parasite (i.e., a parasite that causes malaria) metabolizes (in its digestive vacuole (DV)) hemoglobin present in erythrocytes. A by-product of this metabolic process is heme, which would be toxic to the parasite except for heme detoxification mechanisms developed by the microorganism. CQ is believed to inhibit heme detoxification in the DV by binding to heme and/or to hemozoin (Ginsburg et al, 1999. *Parasitol. Today* 15:357; Chong and Sullivan. 2003. *Biochem. Pharmacol.* 66(11):2201-2212; Leed et al. 2002. *Biochem.* 41(32):10245-10255; Egan et al. 2001. *Biochem.* 40(1):204-213; Raynes. 1999. *Int. J. Parasitol.* 29(3):367-379; Egan et al. 2000. *J. Med. Chem.* 43(2): 283-291; Weissbuch and Leiserowitz. 2008. *Chem. Rev.* 108 (11):4899-4914). This binding, in part, is thought to drive the thermodynamics that concentrates CQ in the parasite DV. Chloroquine-dependent heme accumulation in the DV may inhibit or kill the parasites.

Unfortunately, certain *Plasmodium* strains have evolved resistance to CQ. In fact, the spread of chloroquine-resistant ($CQ^R$) *Plasmodium* parasites has rendered CQ almost useless for malaria treatment. In addition, *Plasmodium* resistance to other antimalarial drugs, such as artemisinin and its derivatives, has been reported (Xiao et al. 2004. *Parasitol. Res.* 92(3):215-219). These are particularly devastating problems in many impoverished parts of the world where such drugs are most needed (Krogstad. 1996. *Epidemiol. Rev.* 18(1):77-89).

*Plasmodium* $CQ^R$ is correlated with mutations in the parasite's DV membrane transporter protein (PfCRT). PfCRT is thought to enhance CQ export from the DV (Zhang et al. 2004. *Biochem.* 43(26):8290-8296; Bennett et al. 2004. *Mol. Biochem. Parasitol.* 133(1): 99-114; Martin and Kirk. 2004. *Mol. Biol. Evol.* 21(10): 1938-1949). A particularly well-studied. PfCRT mutation is K76T, which is correlated with $CQ^R$ (Martin and Kirk. 2004. supra; Johnson et al. 2004. *Mol. Cell.* 15(6):867-877; Durrand et al. 2004. *Mol. Biochem. Parasitol.* 136(2):273-285; Ranjit et al. 2004. *Trop. Med. Int. Health* 9(8):857-861; Durand et al. 2002. *Antimicrob. Agents Chemother.* 46(8):2684-2686; Durand et al. 2001. *Mol. Biochem. Parasitol.* 114(1):95-102; Cooper et al. 2002. *Mol. Pharmacol.* 61(1):35-42; Djimde et al. 2001. *N. Engl. J. Med.* 344(4):257-263, 2001).

Alternative therapies for treatment of chloroquine-resistant ($CQ^R$) malaria parasites have been developed, including combination therapies (Kumar et al. 2003. *Curr. Med. Chem.* 10(13):1137-1150). However, none of these therapies meet CQ's ease of use and low cost.

One approach to treatment of $CQ^R$ parasites involves the use of chemicals known as "reversal agents." Reversal agents are chemicals that have been found to overcome CQ resistance (Krogstad et al., Science, 238(4831):1283-1285, 1987; Martin et al., Science, 235(4791):899-901, 1987; Ryall, Parasitol, Today, 3(8):256, 1987); thus, making $CQ^R$ strains sensitive again to CQ. $CQ^R$ reversal agents do not appear to have independent therapeutic value against *Plasmodium* as shown when a therapeutically useful dose for CQ applied to a $CQ^S$ strain in the presence of a reversal agent is nearly the same as in the absence of the reversal agent. However, despite their effectiveness against $CQ^R$ *Plasmodium* strains in vitro, therapeutically effective doses of many reversal agents would have to be quite high (with associated side effects) to reverse $CQ^R$ in vivo (van Schalkwyk et al., Antimicrob. Agents Chemother., 45(11):3171-3174, 2001; Millet et al., Antimicrob. Agents Chemother., 48(7):2753-2756, 2004).

New compositions and methods for the treatment of malaria, particularly for the treatment of $CQ^R$ malaria parasites, are needed.

SUMMARY OF THE INVENTION

Embodiments of the invention are directed to a compound having the formula $$Q\text{-}L^1\text{-}G \qquad (I),$$

wherein
Q is

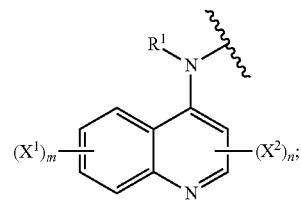

wherein
$X^1$ and $X^2$ are independently selected from alkyl, substituted alkyl, alkoxy, amino, substituted amino, halogen, and hydroxyl;

n is an integer from zero to 2;
m is an integer from zero to 4;
$R^1$ is selected from hydrogen, alkyl, substituted alkyl, sulfonyl, and acyl;
$L^1$ is $C_{1-12}$ alkylene or substituted $C_{1-12}$ alkylene;
G is

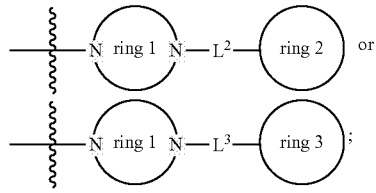

wherein
ring 1 is a heterocyclic ring or substituted heterocyclic ring; and
ring 2 is a monocyclic ring selected from aryl, substituted aryl, heteroaryl, substituted heteroaryl, cycloalkyl, substituted cycloalkyl, heterocyclyl, and substituted heterocyclyl;
ring 3 is a polycyclic ring;
$L^2$ is a bond or $C_{1-12}$ alkylene or substituted $C_{1-12}$ alkylene; and
$L^3$ is substituted $C_{1-12}$ alkylene, wherein the substituted $C_{1-12}$ alkylene is substituted with an oxo group;
or salts or solvates or stereoisomers thereof;
with the provisos:
1) wherein if $L^1$ is $C_2$ alkylene and $L^2$ is a bond and ring 1 is

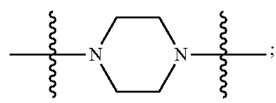 [SMILES: *N1CCN(*)CC1]

then ring 2 is not phenyl or 2-pyridyl;
2) wherein if $L^1$ is $C_2$ alkylene and $L^2$ is $C_2$ alkylene and ring 1 is

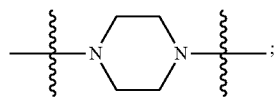

then ring 2 is not 3-diethylamino-4-hydroxy-phenyl;
3) wherein if $L^1$ is $C_2$ alkylene and $L^2$ is a bond and ring 1 is

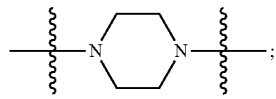

then ring 2 is not a phenyl ring substituted with oxazolidonyl;
4) wherein if $L^1$ is $C_3$ alkylene and $L^2$ is $C_3$ alkylene and ring 1 is

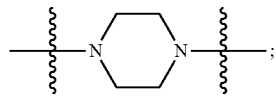

then ring 2 is not pyrrolidyl, piperidyl, or azepanyl;

5) wherein if $L^1$ is $C_2$ alkylene and $L^2$ is $C_3$ or $C_7$ alkylene and ring 1 is

then ring 2 is not substituted piperidyl;
6) wherein if $L^1$ is $C_3$ alkylene and $L^2$ is $C_3$ or $C_6$ alkylene and ring 1 is

then ring 2 is not substituted piperidyl.
In some embodiments of the invention, G is

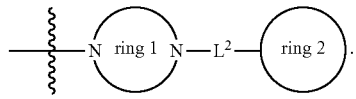

In some embodiments, G is

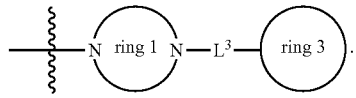

In some embodiments of the invention, m is 1 and $X^1$ is a halogen. In some embodiments, m is zero.
In some embodiments of the invention, $R^1$ is hydrogen. In some embodiments, $R^1$ is $C_{1-4}$ alkyl.
In some embodiments of the invention, n is zero.
In some embodiments of the invention, $L^1$ is $C_{1-4}$ alkylene. In some embodiments, $L^1$ is $C_{2-3}$ alkylene.
In some embodiments of the invention, ring 1 is a 5 to 7-membered ring. In some embodiments, ring 1 is 1,4-piperazinyl; $L^2$ is a bond; and ring 2 is a substituted aryl group, wherein the substituents for the aryl ring are selected from halo, alkoxy, and trifluoromethyl. In some embodiments, the substituents for the aryl ring are selected from chloro, fluoro, methoxy, and trifluoromethyl. In some embodiments, ring 1 is 1,4-piperazinyl; $L^2$ is a bond; and ring 2 is an aryl group. In some embodiments, ring 1 is 1,4-piperazinyl; $L^2$ is a bond; and ring 2 is a pyridinyl group.
In some embodiments of the invention, ring 2 is a ring selected from aryl, substituted aryl, heteroaryl, and substituted heteroaryl.
In some embodiments of the invention, ring 2 is a ring selected from phenyl, substituted phenyl, pyridyl, pyrrolyl, pyrazolyl, imidazolyl, pyrazinyl, pyrimidinyl, pyridazinyl, triazolyl, and tetrazolyl. In some embodiments, ring 2 is a ring that is substituted phenyl, wherein the substituents are selected from hydroxy, alkyl, alkoxy, cycloalkyl, cycloalkenyl, substituted alkyl, substituted alkoxy, substituted cycloalkyl, substituted cycloalkenyl, amino, substituted amino, aryl, halo, heteroaryl, heteroaryloxy, heterocyclic, and heterocyclooxy. In some embodiments, ring 2 is a ring that is substituted phenyl, wherein the substituents are selected from halo, alkoxy, alkyl, substituted alkyl, aryl, substituted aryl, cycloalkyl, and substituted cycloalkyl.

In some embodiments of the invention, the compounds have a formula:

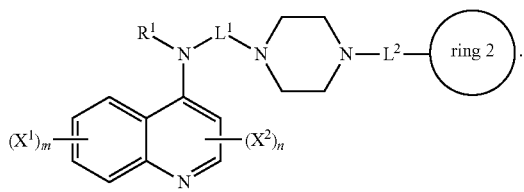

In some embodiments, $L^1$ is $C_{2-3}$ alkylene. In some embodiments, $L^2$ is a bond or a $C_{1-2}$ alkylene. In some embodiments, ring 2 is phenyl, 2-pyridinyl, 3-pyridinyl, or 4-pyridinyl. In some embodiments, ring 2 is a substituted phenyl. In some embodiments, the substituents on the phenyl are selected from halo, alkoxy, alkyl, substituted alkyl, aryl, substituted aryl, cycloalkyl, and substituted cycloalkyl.

In some embodiments of the invention, the compounds have a formula:

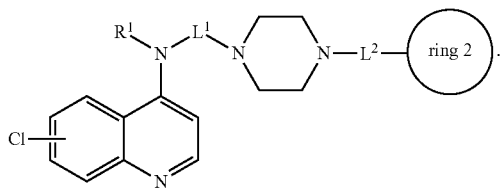

In some embodiments of the invention, the compounds have a formula:

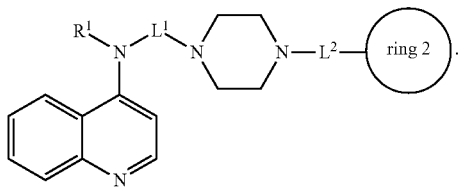

Embodiments of the invention are also related to a compound selected from: 7-chloro-N-(3-(4-phenylpiperazin-1-yl)propyl)quinolin-4-amine; 7-chloro-N-(3-(4-(pyridin-2-yl)piperazin-1-yl)propyl)quinolin-4-amine; 7-chloro-N-(3-(4-(pyridin-4-yl)piperazin-1-yl)propyl)quinolin-4-amine; 7-chloro-N-(3-(4-(4-fluorophenyl)piperazin-1-yl)propyl)quinolin-4-amine; 7-chloro-N-(3-(4-(4-methoxyphenyl)piperazin-1-yl)propyl)quinolin-4-amine; 7-chloro-N-(3-(4-(4-(trifluoromethyl)phenyl)piperazin-1-yl)propyl)quinolin-4-amine; 7-chloro-N-(3-(4-(4-chlorophenyl)piperazin-1-yl)propyl)quinolin-4-amine; 7-chloro-N-(3-(4-(3,4-dichlorophenyl)piperazin-1-yl)propyl)quinolin-4-amine; N-(3-(4-(biphenyl-4-yl)piperazin-1-yl)propyl)-7-chloroquinolin-4-amine; N-(3-(4-(biphenyl-3-yl)piperazin-1-yl)propyl)-7-chloroquinolin-4-amine; N-(3-(4-(biphenyl-2-yl)piperazin-1-yl)propyl)-7-chloroquinolin-4-amine; 7-chloro-N-(3-(4-phenethylpiperazin-1-yl)propyl)quinolin-4-amine; 7-chloro-N-(3-(4-(naphthalen-1-ylmethyl)piperazin-1-yl)propyl)quinolin-4-amine; 7-chloro-N-(3-(4-p-tolylpiperazin-1-yl)propyl)quinolin-4-amine; 7-chloro-N-(3-(4-(4-nitrophenyl)piperazin-1-yl)propyl)quinolin-4-amine; 7-chloro-N-(3-(4-(pyrimidin-2-yl)piperazin-1-yl)propyl)quinolin-4-amine; N-(3-(4-(4-aminophenyl)piperazin-1-yl)propyl)-7-chloroquinolin-4-amine; 7-chloro-N-(3-(4-(2,4-dinitrophenyl)piperazin-1-yl)propyl)quinolin-4-amine; 7-chloro-N-(3-(4-(5-nitropyridin-2-yl)piperazin-1-yl)propyl)quinolin-4-amine; 7-chloro-N-(3-(4-(5-(trifluoromethyl)pyridin-2-yl)piperazin-1-yl)propyl)quinolin-4-amine; 7-chloro-N-(3-(4-(3,5-dinitropyridin-2-yl)piperazin-1-yl)propyl)quinolin-4-amine; 7-chloro-N-(2-(4-(pyridin-2-yl)piperazin-1-yl)ethyl)quinolin-4-amine; 7-chloro-N-(3-(4-(pyridin-3-yl)piperazin-1-yl)propyl)quinolin-4-amine; 7-chloro-N-(3-(4-(pyridin-4-yl)piperazin-1-yl)propyl)quinolin-4-amine; and salts or solvates or stereoisomers or combinations thereof.

In some embodiments of the invention, a compound selected from the following is provided: 7-chloro-N-(3-(4-(4-fluorophenyl)piperazin-1-yl)propyl)quinolin-4-amine; 7-chloro-N-(3-(4-(4-methoxyphenyl)piperazin-1-yl)propyl)quinolin-4-amine; chloro-N-(3-(4-(4-(trifluoromethyl)phenyl)piperazin-1-yl)propyl)quinolin-4-amine; and 7-chloro-N-(3-(4-(4-chlorophenyl)piperazin-1-yl)propyl)quinolin-4-amine; or salts or solvates or stereoisomers thereof.

In some embodiments of the invention, a compound selected from the following is provided: 7-chloro-N-(3-(4-phenylpiperazin-1-yl)propyl)quinolin-4-amine; and 7-chloro-N-(3-(4-(pyridin-2-yl)piperazin-1-yl)propyl)quinolin-4-amine; or a salt or solvate or stereoisomer thereof.

Embodiments of the invention are directed to a compound having the formula:

$$Q-L^1-G \qquad (I),$$

wherein Q is

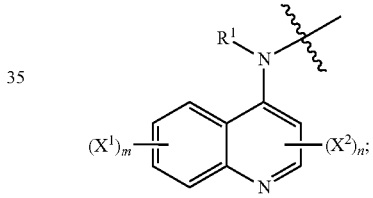

$X^1$ and $X^2$ are independently selected from alkyl, substituted alkyl, alkoxy, amino, substituted amino, halogen, and hydroxyl;

n is an integer from zero to 2;

m is an integer from zero to 4;

$R^1$ is selected from hydrogen, alkyl, substituted alkyl, sulfonyl, and acyl;

$L^1$ is $C_{1-12}$ alkylene or substituted $C_{1-12}$ alkylene;

G is

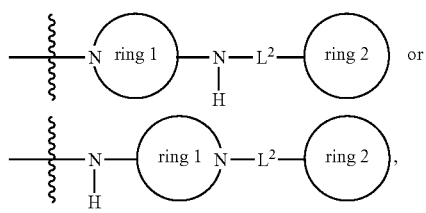

wherein
 ring 1 is a heterocyclic ring or substituted heterocyclic ring,
 ring 2 is a monocyclic ring selected from aryl, substituted aryl, heteroaryl, substituted heteroaryl, cycloalkyl, substituted cycloalkyl, heterocyclyl, and substituted heterocyclyl, and
 $L^2$ is a bond or $C_{1-12}$ alkylene or substituted $C_{1-12}$ alkylene; or salts or solvates or stereoisomers thereof.

Embodiments of the invention are also directed to a compound having the formula:

Q-L¹-G   (I), wherein Q is

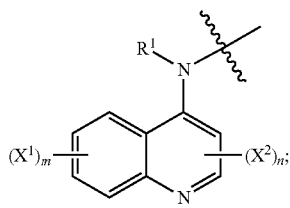

X¹ and X² are independently selected from alkyl, substituted alkyl, alkoxy, amino, substituted amino, halogen, and hydroxyl;
n is an integer from zero to 2;
m is an integer from zero to 4;
R¹ is selected from hydrogen, alkyl, substituted alkyl, sulfonyl, and acyl;
L¹ is $C_{1-12}$ alkylene or substituted $C_{1-12}$ alkylene;
G is

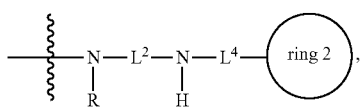

wherein
L² is $C_{1-12}$ alkylene or substituted $C_{1-12}$ alkylene,
L⁴ is a bond or $C_{1-2}$ alkylene or substituted $C_{1-2}$ alkylene,
R is hydrogen, methyl, or ethyl, and
ring 2 is a monocyclic ring selected from aryl, substituted aryl, heteroaryl, substituted heteroaryl, cycloalkyl, substituted cycloalkyl, heterocyclyl, and substituted heterocyclyl;
or salts or solvates or stereoisomers thereof.

In some embodiments of the invention, the salt is a pharmaceutically acceptable salt.

Embodiments of the invention are related to a pharmaceutical composition containing a compound as herein described and a pharmaceutically acceptable carrier.

Embodiments of the invention are also related to a pharmaceutical composition comprising a compound having the formula:

Q-L¹-G   (I), wherein
Q is

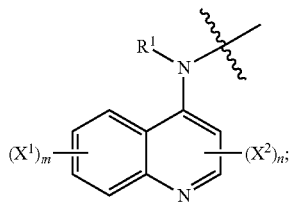

wherein
X¹ and X² are independently selected from alkyl, substituted alkyl, alkoxy, amino, substituted amino, halogen, and hydroxyl;
n is an integer from zero to 2;
m is an integer from zero to 4;
R¹ is selected from hydrogen, alkyl, substituted alkyl, sulfonyl, and acyl;
L¹ is $C_{1-12}$ alkylene or substituted $C_{1-12}$ alkylene;
G is

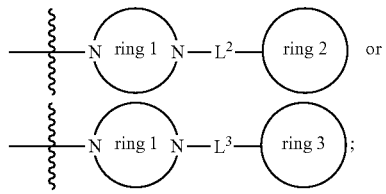

wherein
ring 1 is a heterocyclic ring or substituted heterocyclic ring; and
ring 2 is a monocyclic ring selected from aryl, substituted aryl, heteroaryl, substituted heteroaryl, cycloalkyl, substituted cycloalkyl, heterocyclyl, and substituted heterocyclyl;
ring 3 is a polycyclic ring;
L² is a bond or $C_{1-12}$ alkylene or substituted $C_{1-12}$ alkylene; and
L³ is substituted $C_{1-12}$ alkylene, wherein the substituted $C_{1-12}$ alkylene is substituted with an oxo group;
with the provisos:
1) wherein if L¹ is $C_2$ alkylene and L² is $C_2$ alkylene and ring 1 is

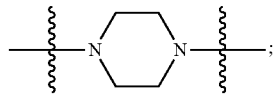

then ring 2 is not 3-diethylamino-4-hydroxy-phenyl;
2) wherein if L¹ is $C_2$ alkylene and L² is a bond and ring 1 is

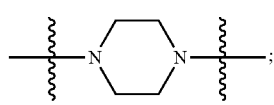 [SMILES: *N1CCN(*)CC1]

then ring 2 is not a phenyl ring substituted with oxazolidonyl;
3) wherein if L¹ is $C_3$ alkylene and L² is $C_3$ alkylene and ring 1 is

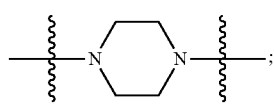

then ring 2 is not pyrrolidyl, piperidyl, or azepanyl;
4) wherein if L¹ is $C_2$ alkylene and L² is $C_3$ or $C_7$ alkylene and ring 1 is

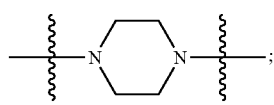

then ring 2 is not substituted piperidyl;

5) wherein if $L^1$ is $C_3$ alkylene and $L^2$ is $C_3$ or $C_6$ alkylene and ring 1 is

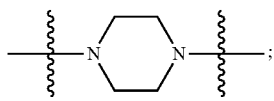

then ring 2 is not substituted piperidyl;
or a pharmaceutically acceptable salt or solvate or stereoisomer thereof;
and a pharmaceutically acceptable carrier.

Embodiments of the invention are also directed to a kit containing a compound as herein described.

In embodiments of the invention, a method for inhibiting the growth of a CQ-susceptible microorganism is provided, the method comprising contacting at least one CQ-susceptible microorganism with a growth inhibiting amount of a compound as herein described. In some embodiments, the CQ-susceptible microorganism is *Plasmodium*. In some embodiments, the CQ-susceptible microorganism is in blood.

Embodiments of the invention also include the provision of a method for inhibiting or treating a disease or condition caused by a CQ-susceptible microorganism in a subject, the method comprising administering to the subject a compound as herein described. In some embodiments, the disease or condition is malaria.

In embodiments of the invention, the use of a compound as herein described is provided for the manufacture of a medicament for the treatment of a disease or condition caused by a CQ-susceptible microorganism in a subject.

Embodiments of the invention also provide a compound as herein described for use in the treatment of a disease or condition caused by a CQ-susceptible microorganism in a subject.

Embodiments of the invention are directed to a method of studying a biological system or sample containing a CQ-susceptible microorganism, the method including: (a) contacting the biological system or sample with a compound as herein described; and (b) determining the inhibiting effects caused by the compound on the biological system or sample.

In embodiments of the invention, a method of generating comparison data is provided, the method including: (a) conducting a biological assay with a test compound to provide a first assay value; (b) conducting the biological assay with a compound as herein described; wherein step (a) is conducted either before, after or concurrently with step (b); and (c) comparing the first assay value from step (a) with the second assay value from step (b) to generate the comparison data. In some embodiments, the biological assay is selected from inhibition, cytotoxicity, and bioavailability.

Embodiments of the invention are also related to a method of preparing a compound of formula:

Q-L$^1$-G    (I), wherein Q is

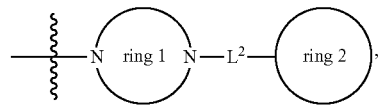

$X^1$ and $X^2$ are independently selected from alkyl, substituted alkyl, alkoxy, amino, substituted amino, halogen, and hydroxyl;

n is an integer from zero to 2;
m is an integer from zero to 4;
$R^1$ is selected from hydrogen, alkyl, substituted alkyl, sulfonyl, and acyl;
$L^1$ is $C_{1-12}$ alkylene or substituted $C_{1-12}$ alkylene; and
G is

wherein
ring 1 is a heterocyclic ring or substituted heterocyclic ring,
ring 2 is a monocyclic ring selected from aryl, substituted aryl, heteroaryl, substituted heteroaryl, cycloalkyl, substituted cycloalkyl, heterocyclyl, and substituted heterocyclyl, and
$L^2$ is a bond or $C_{1-12}$ alkylene or substituted $C_{1-12}$ alkylene, with the provisos:
1) wherein if $L^1$ is $C_2$ alkylene and $L^2$ is a bond and ring 1 is

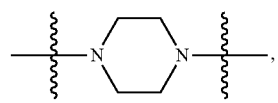

then ring 2 is not phenyl or 2-pyridyl;
2) wherein if $L^1$ is $C_2$ alkylene and $L^2$ is $C_2$ alkylene and ring 1 is

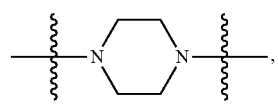

then ring 2 is not 3-diethylamino-4-hydroxy-phenyl;
3) wherein if $L^1$ is $C_2$ alkylene and $L^2$ is a bond and ring 1 is

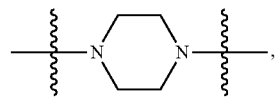

then ring 2 is not a phenyl ring substituted with oxazolidonyl;
4) wherein if $L^1$ is $C_3$ alkylene and $L^2$ is $C_3$ alkylene and ring 1 is

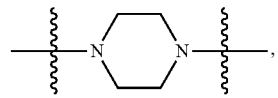 [SMILES: *N1CCN(*)CC1]

then ring 2 is not pyrrolidyl, piperidyl, or azepanyl;
5) wherein if $L^1$ is $C_2$ alkylene and $L^2$ is $C_3$ or $C_7$ alkylene and ring 1 is

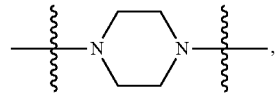 [SMILES: *N1CCN(*)CC1]

then ring 2 is not substituted piperidyl;

6) wherein if $L^1$ is $C_3$ alkylene and $L^2$ is $C_3$ or $C_6$ alkylene and ring 1 is

then ring 2 is not substituted piperidyl,
the method including:
contacting a compound of formula

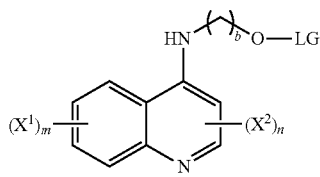

with a compound of formula

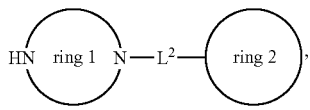

wherein O-LG represents an activated leaving group.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
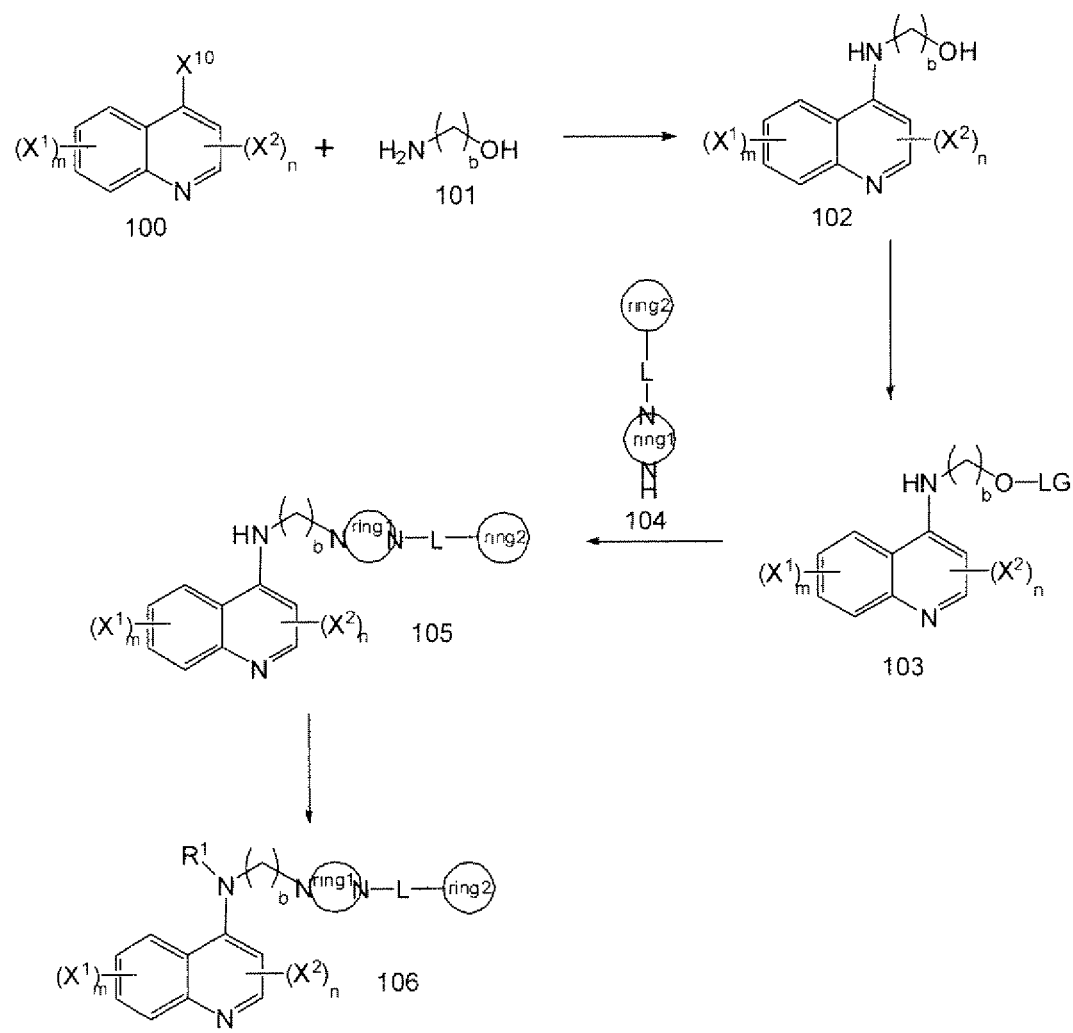
FIG. 1 illustrates a schematic of a representative synthesis protocol for a compound of formula I.

Disclosed herein are compounds that have been discovered that are highly effective against CQ-susceptible microorganisms. Such compounds can be used, at least, in pharmaceutical compositions, and to inhibit or treat diseases or conditions caused by CQ-susceptible microorganisms.

Embodiments of the invention are directed to modified chloroquine compounds. Embodiments of the invention also relate to pharmaceutical compositions comprising such compounds, methods of using such compounds to inhibit or treat diseases or conditions caused by CQ-susceptible microorganisms, and processes and intermediates useful for preparing such compounds.

Any of the foregoing or other disclosed compounds can be incorporated into pharmaceutical compositions that include a therapeutically effective amount of the compound and a pharmaceutically acceptable carrier. In some instances, a disclosed pharmaceutical composition can further include at least one antimalarial agent or other therapeutic agent (such as, for example, artesunate, mefloquine, sulfadoxine, or pyrimethamine, or combinations thereof).

The present disclosure also relates to methods of inhibiting or treating diseases or conditions caused by a CQ-susceptible microorganism in a subject by administering to the subject a therapeutically effective amount of any of the compounds disclosed herein. In some cases, such a compound is administered prophylactically. In other embodiments, such a compound is administered to ameliorate, suppress, or alleviate symptoms of an existing disease. In some cases, the CQ-susceptible microorganism can be a malarial pathogen, such as *P. falciparum*.

Also disclosed are methods for inhibiting the growth of a CQ-susceptible microorganism involving contacting at least one CQ-susceptible microorganism with an amount of at least one disclosed compound sufficient to inhibit growth of the at least one CQ-susceptible microorganism. Exemplary growth-inhibitory amounts can be about 100 nM, about 75 nM, about 50 nM, about 25 nM, about 10 nM or less. In some methods, the CQ-susceptible microorganism is *Plasmodium*. In some method embodiments, the *Plasmodium* is *P. falciparum, P. vivax, P. ovate*, or *P. malariae*, or a combination thereof.

Definitions

Unless otherwise noted, terms are to be understood according to conventional usage by those of ordinary skill in the relevant art. For example, definitions of common terms in chemistry terms may be found in *The McGraw-Hill Dictionary of Chemical Terms*, 1985, and *The Condensed Chemical Dictionary*, 1981.

As used herein, the term "pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically acceptable inorganic or organic acids.

The term "salt thereof" means a compound formed when the hydrogen of an acid is replaced by a cation, such as a metal cation or an organic cation and the like or when a base is protonated with a hydrogen and accompanying anion, such as a non-organic anion or an organic anion and the like. In some embodiments, the salt is a pharmaceutically acceptable salt, although this is not required for salts of intermediate compounds that are not intended for administration to a patient.

The term "solvate" as used herein refers to a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a salt or solvate or stereoisomer thereof" or "or salts or solvates or stereoisomers thereof" is intended to include all permutations of salts, solvates and stereoisomers, such as a solvate of a salt of a stereoisomer of a compound of formula I.

The term "therapeutically effective amount" means an amount sufficient to effect treatment when administered to a patient in need of treatment.

The term "treating" or "treatment" as used herein means the treating or treatment of a disease or medical condition in a subject, such as a mammal (including, for example, a human, a companion animal or a zoo animal) that includes: (a) preventing the disease or medical condition from occurring, i.e., prophylactic treatment of a subject; (b) ameliorating the disease or medical condition, i.e., eliminating or causing regression of the disease or medical condition in a subject; (c)

suppressing the disease or medical condition, i.e., slowing or arresting the development of the disease or medical condition in a subject; or (d) alleviating the symptoms of the disease or medical condition in a subject.

As used herein, the term "subject" includes all animals, including humans and other animals, including, but not limited to, companion animals, farm animals and zoo animals. The term "animal" can include any living multi-cellular vertebrate organisms, a category that includes, for example, a mammal, a bird, a simian, a dog, a cat, a horse, a cow, a rodent, and the like. Likewise, the term "mammal" includes both human and non-human mammals.

As used herein, the term "optional" means that the subsequently described event or circumstance can but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or disubstituted with an alkyl group and situations where the heterocyclo group is not substituted with the alkyl group.

It is further to be understood that any molecular weight or molecular mass values are approximate and are provided only for description.

Except as otherwise noted, the methods and techniques of the present invention are generally performed according to conventional methods well known in the art and as described in various general and more specific references that are cited and discussed throughout the present specification. See, e.g., Loudon, *Organic Chemistry*, Fourth Edition, New York: Oxford University Press, 2002, pp. 360-361, 1084-1085; Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978.

The nomenclature used herein to name the compounds is illustrated in the Examples herein. This nomenclature has generally been derived using the commercially-available AutoNom software (MDL, San Leandro, Calif.).

Abbreviations and Terms
CQ: chloroquine
$CQ^R$: chloroquine resistant (or chloroquine resistance)
$CQ^S$: chloroquine sensitive
DV: digestive vacuole
$IC_{50}$: concentration of an agent resulting in 50% inhibition of microorganism growth
MCQ: modified chloroquine Representative Embodiments: Compounds The following substituents and values are intended to provide representative examples of various aspects and embodiments. These representative values are intended to further define and illustrate such aspects and embodiments and are not intended to exclude other embodiments or to limit the scope of this invention. In this regard, the description of a particular value or substituent in disclosed embodiments is not intended in any way to exclude other values or substituents from this invention unless specifically indicated.

These compounds can contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers can be present in the compositions unless otherwise indicated, provided that the desired utility of the composition as a whole is not eliminated by the presence of such other isomers.

Embodiments of the invention relate to compounds that are effective against CQ-susceptible microorganisms, such as $CQ^R$ and/or $CQ^S$ malaria parasites. Such compounds can be used, at least, in pharmaceutical compositions, and to inhibit or treat diseases or conditions caused by a CQ-susceptible microorganism such as malaria and to inhibit the growth of *Plasmodium*.

Accordingly, in embodiments of the invention, a compound of formula I is provided:

Q-L$^1$-G        (I), wherein
Q is

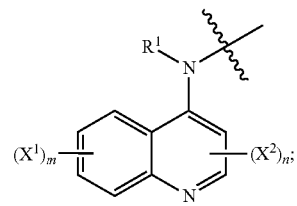

wherein
$X^1$ and $X^2$ are independently selected from alkyl, substituted alkyl, alkoxy, amino, substituted amino, halogen, and hydroxyl;
n is an integer from zero to 2;
m is an integer from zero to 4;
$R^1$ is selected from hydrogen, alkyl, substituted alkyl, sulfonyl, and acyl;
$L^1$ is $C_{1-12}$ alkylene or substituted $C_{1-12}$ alkylene;
G is

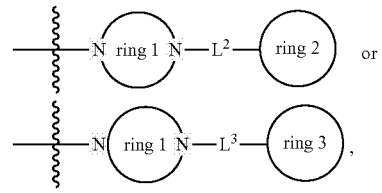

wherein
ring 1 is a heterocyclic ring or substituted heterocyclic ring; and
ring 2 is a monocyclic ring selected from aryl, substituted aryl, heteroaryl, substituted heteroaryl, cycloalkyl, substituted cycloalkyl, heterocyclyl, and substituted heterocyclyl;
ring 3 is a polycyclic ring;
$L^2$ is a bond or $C_{1-12}$ alkylene or substituted $C_{1-12}$ alkylene; and
$L^3$ is substituted $C_{1-12}$ alkylene, wherein the substituted $C_{1-12}$ alkylene is substituted with an oxo group;
or a salt or solvate or stereoisomer thereof.

The following provisos can apply to formula I with regard to compounds per se when G is

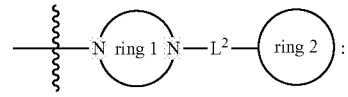

1) if $L^1$ is $C_2$ alkylene and $L^2$ is a bond and ring 1 is

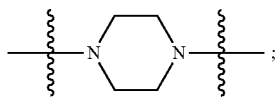

then ring 2 is not phenyl or 2-pyridyl;
2) if $L^1$ is $C_2$ alkylene and $L^2$ is $C_2$ alkylene and ring 1 is

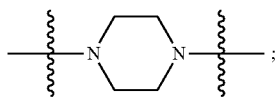 [SMILES: *N1CCN(*)CC1]

then ring 2 is not 3-diethylamino-4-hydroxy-phenyl;
3) if $L^1$ is $C_2$ alkylene and $L^2$ is a bond and ring 1 is

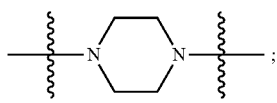 [SMILES: *N1CCN(*)CC1]

then ring 2 is not a phenyl ring substituted with oxazolidonyl;
4) if $L^1$ is $C_3$ alkylene and $L^2$ is $C_3$ alkylene and ring 1 is

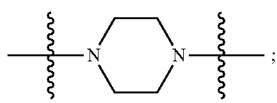

then ring 2 is not pyrrolidyl, piperidyl, or azepanyl;
5) if $L^1$ is $C_2$ alkylene and $L^2$ is $C_3$ or $C_7$ alkylene and ring 1 is

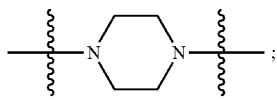

then ring 2 is not substituted piperidyl;
6) if $L^1$ is $C_3$ alkylene and $L^2$ is $C_3$ or $C_6$ alkylene and ring 1 is

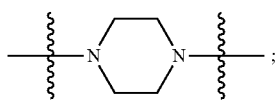

then ring 2 is not substituted piperidyl.

In some embodiments of the invention, a compound of formula I is provided:

Q-L¹-G  (I), wherein
Q is

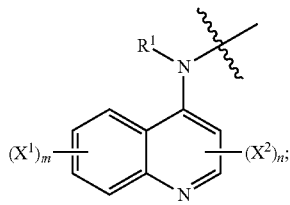

wherein
$X^1$ and $X^2$ are independently selected from alkyl, substituted alkyl, alkoxy, amino, substituted amino, halogen, and hydroxyl;
n is an integer from zero to 2;
m is an integer from zero to 4;
$R^1$ is selected from hydrogen, alkyl, substituted alkyl, sulfonyl, and acyl;
$L^1$ is $C_{1-12}$ alkylene or substituted $C_{1-12}$ alkylene;
G is

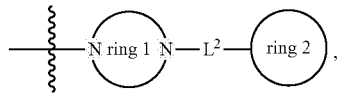

wherein
ring 1 is a heterocyclic ring or substituted heterocyclic ring;
ring 2 is a monocyclic ring selected from aryl, substituted aryl, heteroaryl, substituted heteroaryl, cycloalkyl, substituted cycloalkyl, heterocyclyl, and substituted heterocyclyl; and
$L^2$ is a bond or $C_{1-12}$ alkylene or substituted $C_{1-12}$ alkylene;
or a salt or solvate or stereoisomer thereof.
In some embodiments, G is

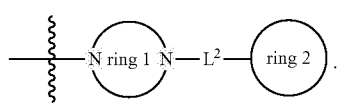

Thus, for example, embodiments of Q-L¹-G can include a compound having a structure as illustrated in formula Ia:

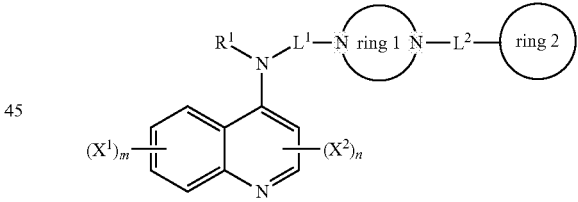

(Ia)

Embodiments of the invention also include the provision of a compound of formula I:

Q-L¹-G  (I), wherein
Q is

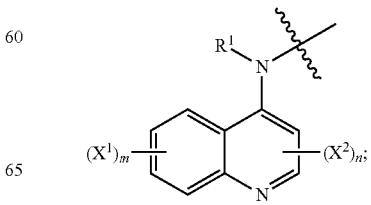

wherein

X¹ and X² are independently selected from alkyl, substituted alkyl, alkoxy, amino, substituted amino, halogen, and hydroxyl;

n is an integer from zero to 2;

m is an integer from zero to 4;

$R^1$ is selected from hydrogen, alkyl, substituted alkyl, sulfonyl, and acyl;

$L^1$ is $C_{1-12}$ alkylene or substituted $C_{1-12}$ alkylene;

G is

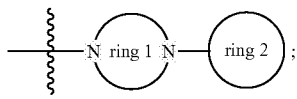

wherein ring 1 is a heterocyclic ring or substituted heterocyclic ring; and ring 2 is a monocyclic ring selected from aryl, substituted aryl, heteroaryl, substituted heteroaryl, cycloalkyl, substituted cycloalkyl, heterocyclyl, and substituted heterocyclyl; wherein if $L^1$ is $C_2$ alkylene and ring 1 is

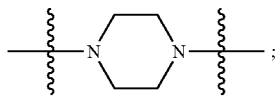

then ring 2 is not phenyl or 2-pyridyl;

or a salt or solvate or stereoisomer thereof.

In some embodiments, $L^2$ is a bond. Thus, for example, embodiments of $Q-L^1-G$ can include a compound having the structure illustrated in formula Ib:

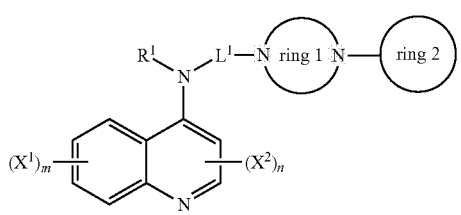

$X^1$ can be selected from alkyl, substituted alkyl, alkoxy, amino, substituted amino, halogen, and hydroxyl. In some embodiments, $X^1$ is selected from alkyl, substituted alkyl, alkoxy, halogen, and hydroxyl. In some embodiments, $X^1$ is alkyl or substituted alkyl, such as, for example, methyl, ethyl, propyl, trifluoromethyl. In some embodiments, $X^1$ is hydroxyl or alkoxy. In some embodiments, $X^1$ can be a halogen, such as, for example, fluoro, chloro, bromo, or iodo. In some embodiments, $X^1$ is chloro. In some embodiments, $X^1$ is fluoro.

$X^2$ can be selected from alkyl, substituted alkyl, alkoxy, amino, substituted amino, halogen, and hydroxyl. In some embodiments, $X^2$ is alkyl or substituted alkyl, such as, for example, methyl, ethyl, propyl, trifluoromethyl. In some embodiments, $X^2$ is amino or substituted amino, such as, for example, amino, methylamino, dimethylamino, ethylamino. In some embodiments, $X^2$ is hydroxyl or alkoxy. In some embodiments, $X^2$ can be a halogen, such as, for example, fluoro, chloro, bromo, or iodo. In some embodiments, $X^2$ is chloro. In some embodiments, $X^2$ is fluoro.

The value for n can range from zero to 2. In some embodiments, n is zero. In some embodiments, n is one. In some embodiments, n is 2.

The value for m can range from zero to 4. In some embodiments, m is zero or one. In some embodiments, m is zero. In some embodiments, m is one.

$R^1$ can be selected from hydrogen, alkyl, substituted alkyl, sulfonyl, and acyl. In some embodiments, $R^1$ is hydrogen. In some embodiments, $R^1$ is $C_{1-4}$ alkyl.

$L^1$ can be $C_{1-12}$ alkylene or substituted $C_{1-12}$ alkylene. In some embodiments, $L^1$ is $C_{1-8}$ alkylene, $C_{1-6}$ alkylene, $C_{1-4}$ alkylene, or $C_{2-3}$ alkylene. In some embodiments, $L^1$ is $C_{1-4}$ alkylene. In some embodiments, $L^1$ is $C_{2-3}$ alkylene. In some embodiments, $L^1$ is $C_2$ alkylene. In some embodiments, $L^1$ is $C_3$ alkylene. In some embodiments, $L^1$ is $C_4$ alkylene.

In some embodiments, $L^1$ is a substituted $C_{1-12}$ alkylene. In some embodiments, the substituted $C_{1-12}$ alkylene is substituted with an oxo group. In some embodiments, $L^1$ is substituted $C_{1-8}$ alkylene, substituted $C_{1-6}$ alkylene, or substituted $C_{1-4}$ alkylene.

Ring 1 can be a heterocyclic ring or substituted heterocyclic ring. As disclosed herein, ring 1 contains two nitrogens. In some embodiments, ring 1 is a 4 to 10-membered heterocyclic ring containing two nitrogens. In some embodiments, ring 1 is a 5 to 7-membered heterocyclic ring containing two nitrogens. In some embodiments, ring 1 is a 6-membered heterocyclic ring containing two nitrogens. In some embodiments, the nitrogens are oriented para to each other in a 6-membered heterocyclic ring.

In embodiments of the invention, ring 1 is a substituted heterocyclic ring. In some embodiments, ring 1 is a 4 to 10-membered substituted heterocyclic ring containing two nitrogens. In some embodiments, ring 1 is a 5 to 7-membered substituted heterocyclic ring containing two nitrogens.

In embodiments having a structure as illustrated in formulas Ia and Ib, ring 2 can be a monocyclic ring selected from aryl, substituted aryl, heteroaryl, substituted heteroaryl, cycloalkyl, substituted cycloalkyl, heterocyclyl, and substituted heterocyclyl. In some embodiments, ring 2 is an aryl or substituted aryl ring. An exemplary aryl ring is phenyl. Other exemplary aryl rings include, but are not limited to, 10-, 14-, and 18-membered aryl rings.

In some embodiments, the aryl ring is substituted with groups. Exemplary substituents for the aryl ring include, but are not limited to, hydroxy, thiol, acyl, alkyl, alkoxy, cycloalkyl, cycloalkenyl, substituted alkyl, substituted alkoxy, substituted cycloalkyl, substituted cycloalkenyl, amino, substituted amino, aryl, aryloxy, cyano, halo, nitro, heteroaryl, heteroaryloxy, heterocyclic, and heterocyclooxy. In some embodiments, the substituent for the phenyl ring is selected from hydroxy, alkyl, alkoxy, cycloalkyl, cycloalkenyl, substituted alkyl, substituted alkoxy, substituted cycloalkyl, substituted cycloalkenyl, amino, substituted amino, aryl, halo, heteroaryl, heteroaryloxy, heterocyclic, and heterocyclooxy. In some embodiments, the substituent for the phenyl ring is selected from halo, alkoxy, alkyl, substituted alkyl, aryl, substituted aryl, cycloalkyl, and substituted cycloalkyl.

In embodiments having a structure as illustrated in formulas Ia and Ib, ring 2 can be a heteroaryl or substituted heteroaryl ring. In some embodiments, ring 2 is 5 to 10 membered ring having one to three heteroatoms selected from N, O, or S. In some embodiments, ring 2 is a nitrogen containing ring. In some embodiments, ring 2 is a heteroaryl that can be, but is not limited to pyridyl, pyrrolyl, thiophene, pyrazolyl, thiazolyl, imidazolyl, pyrimidinyl, thiadiazolyl, indolyl, carbazolyl, azaindolyl, benzofuranyl, benzimidazolyl, benzthiazolyl, quinoxalinyl, benzotriazolyl, benzisoxazolyl, purinyl, quinolinyl, isoquinolinyl, benzopyranyl, pyrazinyl, pyridazinyl, triazolyl, tetrazolyl, and derivatives thereof. In some embodiments, ring 2 is pyridyl, pyrrolyl, pyrazolyl, imidazolyl, pyrazinyl, pyrimidinyl, pyridazinyl, triazolyl, or tetrazolyl. In some embodiments, ring 2 is pyridyl.

In some embodiments, the heteroaryl ring is substituted with groups. Exemplary substituents for the heteroaryl ring can include, but are not limited to, alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$R (where n is an integer from zero to 2 and R is alkyl, haloalkyl, optionally substituted phenyl, amino, or substituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl).

In certain cases for formulas Ia and Ib, ring 2 is a cycloalkyl or substituted cycloalkyl. In some embodiments, ring 2 is 5 to 10 membered cycloalkyl ring. In some embodiments, ring 2 is cyclopentyl, cyclohexyl, or cycloheptyl.

In some embodiments, the cycloalkyl ring is substituted with groups. Certain substituents for the cycloalkyl ring include alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$R (where n is an integer from zero to 2 and R is alkyl, haloalkyl, optionally substituted phenyl, amino, or substituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl).

In some embodiments having a structure as illustrated in formulas Ia and Ib, ring 2 can be a heterocyclyl or substituted heterocyclyl. In some embodiments, ring 2 is a 5- to 10-membered ring having one to three heteroatoms selected from N, O, or S. In some embodiments, ring 2 is a nitrogen containing ring. Representative examples include, but are not limited to, pyrrolidinyl, pyrazolidinyl, imidazolidinyl, piperidinyl, piperazinyl, morpholinyl, tetrahydrofuranyl, tetrahydropyranyl, oxazolidinyl, or thiomorpholinyl.

In some embodiments, the heterocyclyl ring is substituted with groups. Exemplary substituents for the heterocyclyl ring include, but are not limited to, alkyl, haloalkyl, heteroalkyl, aliphatic, heteroaliphatic, alkoxy, halo, cyano, nitro, aryl, optionally substituted heteroaryl, amino, monosubstituted amino, disubstituted amino, hydroxyamino, —OR (where R is hydrogen, haloalkyl, or optionally substituted phenyl), —S(O)$_n$R (where n is an integer from zero to 2 and R is alkyl, haloalkyl, optionally substituted phenyl, amino, or substituted amino), —C(O)R (where R is hydrogen, alkyl, haloalkyl or optionally substituted phenyl), —COOR (where R is hydrogen, alkyl or optionally substituted phenyl), —C(O)N(R')R" (where R' and R" are independently selected from hydrogen, alkyl, haloalkyl, or optionally substituted phenyl).

In embodiments of the invention, $L^2$ is a bond or $C_{1-12}$ alkylene or substituted $C_{1-12}$ alkylene, wherein the substituted $C_{1-12}$ alkylene is substituted with an oxo group. In some embodiments, $L^2$ is a bond. In some embodiments, $L^2$ is $C_{1-8}$ alkylene, $C_{1-6}$ alkylene, $C_{1-4}$ alkylene, or $C_{1-2}$ alkylene. In some embodiments, $L^2$ is a substituted $C_{1-12}$ alkylene. In some embodiments, $L^2$ is substituted $C_{1-8}$ alkylene, substituted $C_{1-6}$ alkylene, substituted $C_{1-4}$ alkylene, or substituted $C_{1-2}$ alkylene. In some embodiments, the substituted $C_{1-12}$ alkylene is substituted with an oxo group.

In some embodiments having a structure as illustrated in formula I, m is one and $X^1$ is halo, such as chloro. In some embodiments, m is zero.

In some embodiments having a structure as illustrated in formula I, n is zero.

In some embodiments having a structure as illustrated in formula I, $R^1$ is hydrogen. In some embodiments, $R^1$ is hydrogen; m is one; and $X^1$ is chloro. In some, embodiments, $R^1$ is hydrogen and m is zero.

In some embodiments having a structure as illustrated in formula I, $L^1$ is $C_3$ alkylene and $R^1$ is hydrogen. In some embodiments, $L^1$ is $C_3$ alkylene, $R^1$ is hydrogen, m is one, and $X^1$ is chloro. In some embodiments, $L^1$ is $C_3$ alkylene, $R^1$ is hydrogen, and m is zero.

In some embodiments having a structure as illustrated in formula I, ring 1 is 1,4-piperazinyl, as shown herein:

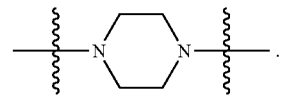

In some embodiments, ring 1 is 1,4-piperazinyl and $L^1$ is $C_3$ alkylene. In some embodiments, ring 1 is 1,4-piperazinyl, $L^1$ is $C_3$ alkylene, and $R^1$ is hydrogen.

In some embodiments having a structure as illustrated in, ring 1 is 1,4-piperazinyl and $L^2$ is a bond. In some embodiments, ring 1 is 1,4-piperazinyl, $L^2$ is a bond, and ring 2 is an aryl ring or substituted aryl ring. In some embodiments, ring 1 is 1,4-piperazinyl, $L^2$ is a bond, and ring 2 is an heteroaryl ring.

In some embodiments having a structure as illustrated in formula I, ring 1 is 1,4-piperazinyl, $L^2$ is a bond, and ring 2 is a substituted aryl group, substituted with one or more electron withdrawing groups, such as halo, alkoxy, and trifluoromethyl. In some embodiments, ring 1 is 1,4-piperazinyl, $L^2$ is a bond, and ring 2 is a substituted aryl group, substituted with a group selected from chloro, fluoro, methoxy, and trifluoromethyl.

In some embodiments having a structure as illustrated in, ring 1 is 1,4-piperazinyl, $L^2$ is a bond, and ring 2 is an aryl group.

In some embodiments having a structure as illustrated in formula I, ring 1 is 1,4-piperazinyl, $L^2$ is a bond, and ring 2 is a pyridinyl group.

In some embodiments having a structure as illustrated in formula I, ring 1 is a 6-membered ring. In such embodiments, these compounds can have the formula Ia-i:

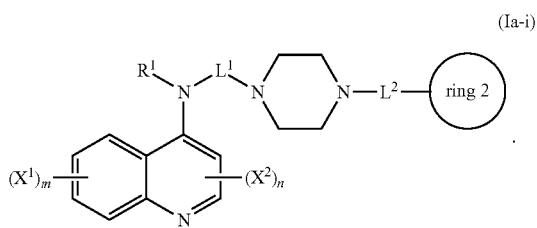
(Ia-i)

In some embodiments having a structure as illustrated in formula I, ring 1 is a 6-membered ring, $X^1$ is chloro, m is one, and n is zero. In such embodiments, these compounds can have the formula Ia-ii:

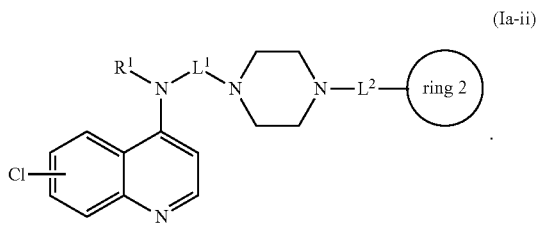
(Ia-ii)

In some embodiments having a structure as illustrated in formula I, ring 1 is a 6-membered ring, m is zero, and n is zero. In such embodiments, these compounds can have the formula Ia-iii:

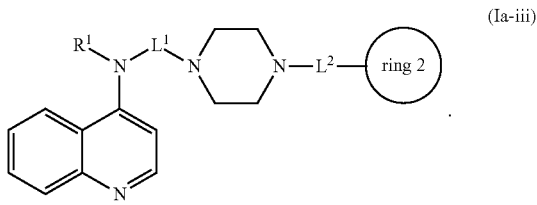
(Ia-iii)

In some embodiments having a structure as illustrated in formula I, wherein ring 1 is a 6-membered ring, $X^1$ is chloro, m is one, n is zero, and $R^1$ is hydrogen. In such embodiments, these compounds can have the formula Ia-iv:

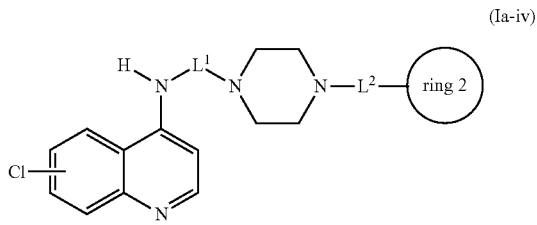
(Ia-iv)

In some embodiments having a structure as illustrated in formula I, ring 1 is a 6-membered ring, m is zero, n is zero, and $R^1$ is hydrogen. In such embodiments, these compounds can have the formula Ia-v:

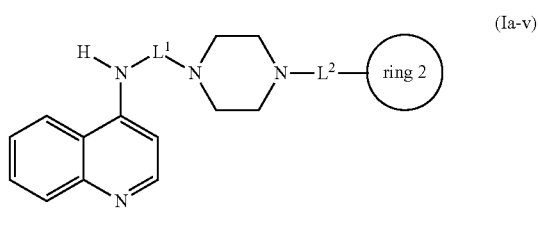
(Ia-v)

In some embodiments having a structure as illustrated in formula I, $L^2$ is a bond and ring 1 is a 6-membered ring. In such embodiments, these compounds can have the formula Ib-i:

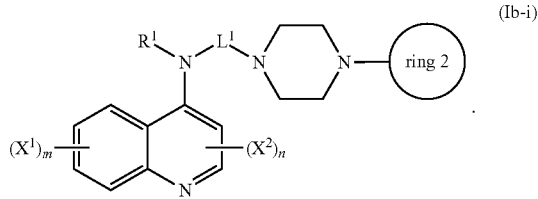
(Ib-i)

In some embodiments having a structure as illustrated in formula I, $L^2$ is a bond and ring 1 is a 6-membered ring, $X^1$ is chloro, m is one, and n is zero. In such embodiments, these compounds can have the formula Ib-ii:

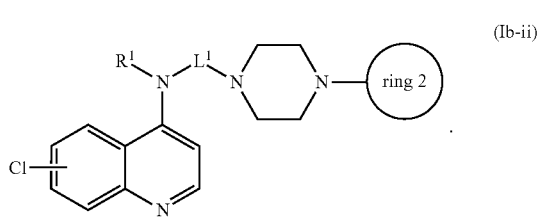
(Ib-ii)

In some embodiments having a structure as illustrated in formula I, $L^2$ is a bond and ring 1 is a 6-membered ring, m is zero, and n is zero. In such embodiments, these compounds can have the formula Ib-iii:

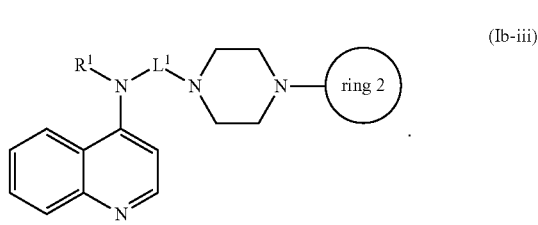
(Ib-iii)

In some embodiments having a structure as illustrated in formula I, $L^2$ is a bond and ring 1 is a 6-membered ring, $X^1$ is chloro, m is one, n is zero, and $R^1$ is hydrogen. In such embodiments, these compounds can have the formula Ib-iv:

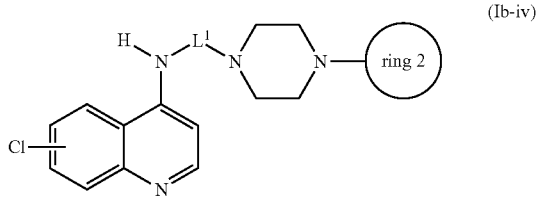
(Ib-iv)

In some embodiments having a structure as illustrated in formula I, wherein L² is a bond and ring 1 is a 6-membered ring, m is zero, n is zero, and R¹ is hydrogen. In such embodiments, these compounds can have the formula Ib-v:

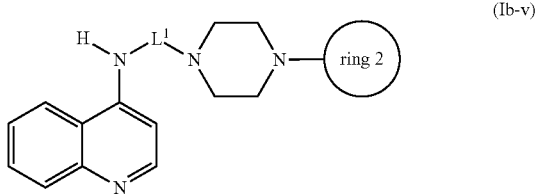
(Ib-v)

Embodiments of the invention also include the provision of a compound of formula I:

Q-L¹-G (I), wherein
Q is

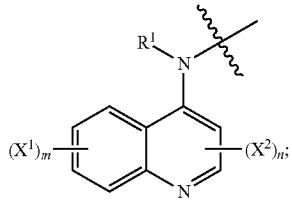

wherein
X¹ and X² are independently selected from alkyl, substituted alkyl, alkoxy, amino, substituted amino, halogen, and hydroxyl;
n is an integer from zero to 2;
m is an integer from zero to 4;
R¹ is selected from hydrogen, alkyl, substituted alkyl, sulfonyl, and acyl;
L¹ is $C_{1-12}$ alkylene or substituted $C_{1-12}$ alkylene;
G is

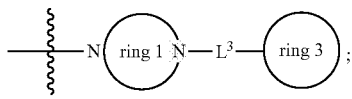;

wherein
ring 1 is a heterocyclic ring or substituted heterocyclic ring; and
ring 3 is a polycyclic ring; and
L³ is substituted $C_{1-12}$ alkylene, wherein the substituted $C_{1-12}$ alkylene is substituted with an oxo group;
or a salt or solvate or stereoisomer thereof.

In some embodiments having a structure as illustrated in formula I, G is

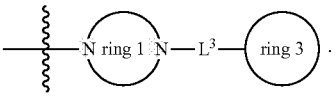.

For example, embodiments of the invention can have the structure as illustrated in formula Ic:

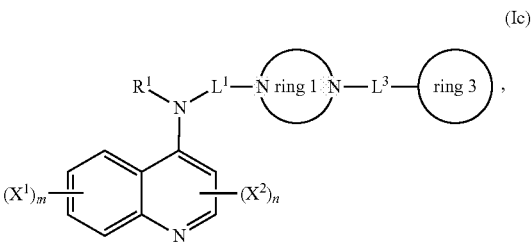
(Ic)

where ring 3 is a polycyclic ring.

In some embodiments having a structure as illustrated in formula Ic, L³ is substituted $C_{1-12}$ alkylene, wherein the substituted $C_{1-12}$ alkylene is substituted with an oxo group. In some embodiments, L³ is $C_{1-8}$ alkylene, $C_{1-6}$ alkylene, $C_{1-4}$ alkylene, or $C_{1-2}$ alkylene. In some embodiments, L³ is a substituted $C_{1-12}$ alkylene, wherein the substituted $C_{1-12}$ alkylene is substituted with an oxo group. In some embodiments, L³ is substituted $C_{1-8}$ alkylene, substituted $C_{1-6}$ alkylene, substituted $C_{1-4}$ alkylene, or substituted $C_{1-2}$ alkylene.

In some embodiments having a structure as illustrated in formula Ic, ring 3 is a polycyclic ring that includes fused cyclic structures having two or more component rings that are saturated or unsaturated. In some embodiments, ring 3 is a tricyclic ring, such as a ring system containing three independently carbocyclic or heterocyclic rings including a central ring and two peripheral rings. Each peripheral ring is fused to the central ring, but neither peripheral ring is fused to the other. Each peripheral ring is aromatic (e.g., phenyl) and can be unsubstituted or substituted as described above for a phenyl group. For example, the substituent for the phenyl ring can be selected from hydroxy, alkyl, alkoxy, cycloalkyl, cycloalkenyl, substituted alkyl, substituted alkoxy, substituted cycloalkyl, substituted cycloalkenyl, amino, substituted amino, aryl, halo, heteroaryl, heteroaryloxy, heterocyclic, and heterocyclooxy. In some embodiments, the substituent for the phenyl ring is selected from halo, alkoxy, alkyl, substituted alkyl, aryl, substituted aryl, cycloalkyl, and substituted cycloalkyl. The central ring can be aromatic or aliphatic, unsaturated or partially saturated (for example, with bridgehead carbons being unsaturated and one or more other ring bonds being saturated), and can be unsubstituted or substituted as described for carbocyclic or heterocyclic rings (and as valence rules allow). For example, heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO₂-alkyl, —SO₂-substituted alkyl, —SO₂-aryl and —SO₂-heteroaryl. Non-limiting examples of a tricyclic ring system include N-xanthenyl, N-phenothiazinyl, N-phenoxazinyl, N-carbazolyl; 10H-acridin-9-one-10-yl; 5,11-dihydro-dibenzo[a,d]cyclohepten-1,0-one-5-yl; 10,11-dihydro-5H-dibenzo[a,d]cycloheptene-5- yl; 10H-benzo[b][1,8]naphthyridin-5-one-N-yl; 6,11-dihydro-5H-benzo[5,6]cyclohepta[1,2b]pyridine-1-yl.

Embodiments of the invention also include the provision of a compound of formula I:

Q-L¹-G (I), wherein
Q is

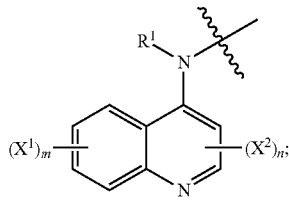

wherein
X¹ and X² are independently selected from alkyl, substituted alkyl, alkoxy, amino, substituted amino, halogen, and hydroxyl;
n is an integer from zero to 2;
m is an integer from zero to 4;
R¹ is selected from hydrogen, alkyl, substituted alkyl, sulfonyl, and acyl;
L¹ is $C_{1-12}$ alkylene or substituted $C_{1-12}$ alkylene, wherein the substituted $C_{1-12}$ alkylene is substituted with an oxo group;
G is

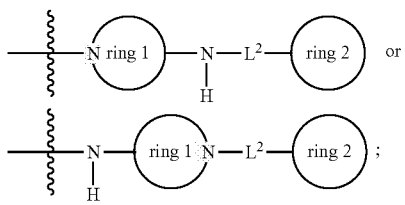

wherein
ring 1 is a heterocyclic ring or substituted heterocyclic ring; and
ring 2 is a monocyclic ring selected from aryl, substituted aryl, heteroaryl, substituted heteroaryl, cycloalkyl, substituted cycloalkyl, heterocyclyl, and substituted heterocyclyl; and
L² is a bond or $C_{1-12}$ alkylene or substituted $C_{1-12}$ alkylene.

Embodiments of the invention also include the provision of a compound of formula I:

Q-L¹-G (I), wherein
Q is

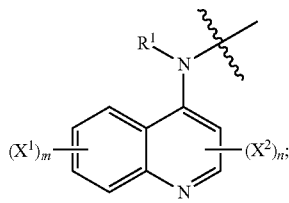

wherein
X¹ and X² are independently selected from alkyl, substituted alkyl, alkoxy, amino, substituted amino, halogen, and hydroxyl;
n is an integer from zero to 2;
m is an integer from zero to 4;
R¹ is selected from hydrogen, alkyl, substituted alkyl, sulfonyl, and acyl;
L¹ is $C_{1-12}$ alkylene or substituted $C_{1-12}$ alkylene, wherein the substituted $C_{1-12}$ alkylene is substituted with an oxo group;
G is

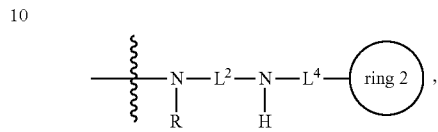

wherein
L² is $C_{1-12}$ alkylene or substituted $C_{1-12}$ alkylene;
L⁴ is a bond or $C_{1-2}$ alkylene or substituted $C_{1-2}$ alkylene;
R is hydrogen, methyl, or ethyl; and
ring 2 is a monocyclic ring selected from aryl, substituted aryl, heteroaryl, substituted heteroaryl, cycloalkyl, substituted cycloalkyl, heterocyclyl, and substituted heterocyclyl.

Exemplary compounds of interest are illustrated in Table 1:

TABLE 1

| Compound # | R¹ | L¹ | G¹ |
|---|---|---|---|
| 1 | —H | —(CH₂)₃— | phenyl |
| 2 | —H | —(CH₂)₃— | 2-pyridyl |
| 3 | —H | —(CH₂)₃— | 4-pyridyl |
| 4 | —H | —(CH₂)₃— | 4-F-phenyl |
| 5 | —H | —(CH₂)₃— | 4-OCH₃-phenyl |
| 6 | —H | —(CH₂)₃— | 4-CF₃-phenyl |
| 7 | —H | —(CH₂)₃— | 4-Cl-phenyl |

TABLE 1-continued

Structure: R¹-N(L¹)-piperazine-G¹ with 7-chloroquinolin-4-yl on N.

| Compound # | R¹ | L¹ | G¹ |
|---|---|---|---|
| 8 | —H | —(CH₂)₃— | 3,4-dichlorophenyl |
| 9 | —H | —(CH₂)₃— | 4-biphenyl |
| 10 | —H | —(CH₂)₃— | 3-biphenyl |
| 11 | —H | —(CH₂)₃— | 2-biphenyl |
| 12 | —H | —(CH₂)₃— | benzyl (—CH₂-phenyl) |
| 13 | —H | —(CH₂)₃— | (naphthalen-1-yl)methyl |
| 14 | —H | —(CH₂)₃— | 4-methylphenyl |
| 15 | —H | —(CH₂)₃— | 4-nitrophenyl |
| 16 | —H | —(CH₂)₃— | pyrimidin-2-yl |
| 17 | —H | —(CH₂)₃— | 4-aminophenyl |
| 18 | —H | —(CH₂)₃— | 2,4-dinitrophenyl |
| 19 | —H | —(CH₂)₃— | 5-nitropyridin-2-yl |
| 20 | —H | —(CH₂)₃— | 5-(trifluoromethyl)pyridin-2-yl |
| 21 | —H | —(CH₂)₃— | 3,5-dinitropyridin-2-yl |
| 22 | —H | —(CH₂)₂— | pyridin-2-yl |
| 23 | —H | —(CH₂)₃— | pyridin-3-yl |
| 24 | —H | —(CH₂)₃— | pyridin-4-yl |

Additional exemplary compounds of interest include:
7-chloro-N-(3-(4-phenylpiperazin-1-yl)propyl)quinolin-4-amine;
7-chloro-N-(3-(4-(pyridin-2-yl)piperazin-1-yl)propyl)quinolin-4-amine;
7-chloro-N-(3-(4-(pyridin-4-yl)piperazin-1-yl)propyl)quinolin-4-amine;
7-chloro-N-(3-(4-(4-fluorophenyl)piperazin-1-yl)propyl)quinolin-4-amine;
7-chloro-N-(3-(4-(4-methoxyphenyl)piperazin-1-yl)propyl)quinolin-4-amine;
7-chloro-N-(3-(4-(4-(trifluoromethyl)phenyl)piperazin-1-yl)propyl)quinolin-4-amine;

7-chloro-N-(3-(4-(4-chlorophenyl)piperazin-1-yl)propyl)
quinolin-4-amine;
7-chloro-N-(3-(4-(3,4-dichlorophenyl)piperazin-1-yl)propyl)quinolin-4-amine;
N-(3-(4-(biphenyl-4-yl)piperazin-1-yl)propyl)-7-chloroquinolin-4-amine;
N-(3-(4-(biphenyl-3-yl)piperazin-1-yl)propyl)-7-chloroquinolin-4-amine;
N-(3-(4-(biphenyl-2-yl)piperazin-1-yl)propyl)-7-chloroquinolin-4-amine;
7-chloro-N-(3-(4-phenethylpiperazin-1-yl)propyl)quinolin-4-amine; and
7-chloro-N-(3-(4-(naphthalen-1-ylmethyl)piperazin-1-yl)propyl)quinolin-4-amine;
7-chloro-N-(3-(4-p-tolylpiperazin-1-yl)propyl)quinolin-4-amine;
7-chloro-N-(3-(4-(4-nitrophenyl)piperazin-1-yl)propyl)quinolin-4-amine;
7-chloro-N-(3-(4-(pyrimidin-2-yl)piperazin-1-yl)propyl)quinolin-4-amine;
N-(3-(4-(4-aminophenyl)piperazin-1-yl)propyl)-7-chloroquinolin-4-amine;
7-chloro-N-(3-(4-(2,4-dinitrophenyl)piperazin-1-yl)propyl)quinolin-4-amine;
7-chloro-N-(3-(4-(5-nitropyridin-2-yl)piperazin-1-yl)propyl)quinolin-4-amine;
7-chloro-N-(3-(4-(5-(trifluoromethyl)pyridin-2-yl)piperazin-1-yl)propyl)quinolin-4-amine;
7-chloro-N-(3-(4-(3,5-dinitropyridin-2-yl)piperazin-1-yl)propyl)quinolin-4-amine;
7-chloro-N-(2-(4-(pyridin-2-yl)piperazin-1-yl)ethyl)quinolin-4-amine;
7-chloro-N-(3-(4-(pyridin-3-yl)piperazin-1-yl)propyl)quinolin-4-amine;
7-chloro-N-(3-(4-(pyridin-4-yl)piperazin-1-yl)propyl)quinolin-4-amine; and
or a salt or solvate or stereoisomer thereof.

In some embodiments, exemplary compounds of interest include:
7-chloro-N-(3-(4-phenylpiperazin-1-yl)propyl)quinolin-4-amine;
7-chloro-N-(3-(4-(pyridin-2-yl)piperazin-1-yl)propyl)quinolin-4-amine;
7-chloro-N-(3-(4-(pyridin-4-yl)piperazin-1-yl)propyl)quinolin-4-amine;
7-chloro-N-(3-(4-(4-fluorophenyl)piperazin-1-yl)propyl)quinolin-4-amine;
7-chloro-N-(3-(4-(4-methoxyphenyl)piperazin-1-yl)propyl)quinolin-4-amine;
7-chloro-N-(3-(4-(4-(trifluoromethyl)phenyl)piperazin-1-yl)propyl)quinolin-4-amine;
7-chloro-N-(3-(4-(4-chlorophenyl)piperazin-1-yl)propyl)quinolin-4-amine;
7-chloro-N-(3-(4-(3,4-dichlorophenyl)piperazin-1-yl)propyl)quinolin-4-amine;
N-(3-(4-(biphenyl-4-yl)piperazin-1-yl)propyl)-7-chloroquinolin-4-amine;
N-(3-(4-(biphenyl-3-yl)piperazin-1-yl)propyl)-7-chloroquinolin-4-amine; and
N-(3-(4-(biphenyl-2-yl)piperazin-1-yl)propyl)-7-chloroquinolin-4-amine;
or a salt or solvate or stereoisomer thereof.

In some embodiments, exemplary compounds of interest include:
7-chloro-N-(3-(4-(4-fluorophenyl)piperazin-1-yl)propyl)quinolin-4-amine;
7-chloro-N-(3-(4-(4-methoxyphenyl)piperazin-1-yl)propyl)quinolin-4-amine;
7-chloro-N-(3-(4-(4-(trifluoromethyl)phenyl)piperazin-1-yl)propyl)quinolin-4-amine; and 7-chloro-N-(3-(4-(4-chlorophenyl)piperazin-1-yl)propyl)quinolin-4-amine;
or a salt or solvate or stereoisomer thereof.

In some embodiments, exemplary compounds of interest include:
7-chloro-N-(3-(4-phenylpiperazin-1-yl)propyl)quinolin-4-amine; and
7-chloro-N-(3-(4-(pyridin-2-yl)piperazin-1-yl)propyl)quinolin-4-amine;
or a salt or solvate or stereoisomer thereof.

Embodiments of the invention are also directed to pharmaceutical compositions comprising a pharmaceutically acceptable carrier and a therapeutically effective amount of a compound of formula I or a pharmaceutically acceptable salt or solvate or stereoisomer thereof. The following provisos can apply to formula I with regard to pharmaceutical compositions when G is

1) if $L^1$ is $C_2$ alkylene and $L^2$ is $C_2$ alkylene and ring 1 is

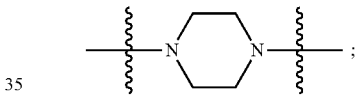

then ring 2 is not 3-diethylamino-4-hydroxy-phenyl;
2) if $L^1$ is $C_2$ alkylene and $L^2$ is a bond and ring 1 is

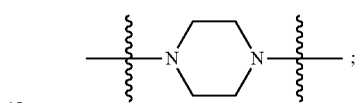

then ring 2 is not a phenyl ring substituted with oxazolidonyl;
3) if $L^1$ is $C_3$ alkylene and $L^2$ is $C_3$ alkylene and ring 1 is

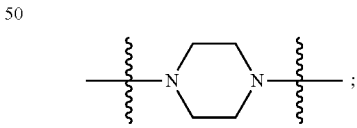

then ring 2 is not pyrrolidyl, piperidyl, or azepanyl;
4) if $L^1$ is $C_2$ alkylene and $L^2$ is $C_3$ or $C_7$ alkylene and ring 1 is

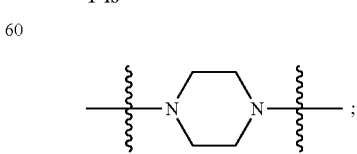

then ring 2 is not substituted piperidyl;

5) if $L^1$ is $C_3$ alkylene and $L^2$ is $C_3$ or $C_6$ alkylene and ring 1 is

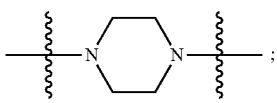

then ring 2 is not substituted piperidyl;

In some embodiments, the pharmaceutical compositions can optionally contain other therapeutic agents. Accordingly, in some embodiments, the pharmaceutical composition further comprises a therapeutically effective amount of an agent selected from artesunate, mefloquine, sulfadoxine, and pyrimethamine.

The compounds are also useful for reducing growth of a CQ-susceptible microorganism. CQ-susceptible microorganisms can include $CQ^R$ and $CQ^S$ malaria parasites. Not being bound by theory, the compounds appear to disrupt the metabolic processes in a malaria parasite, such as by inhibiting heme detoxification or altering the pH. Accordingly, the compounds are useful for treating diseases or conditions caused by CQ-susceptible microorganism such as malaria. The compounds are also useful for reducing growth of *Plasmodium*. The following provisos can apply to formula I with regard to methods of using compounds of formula I when G is

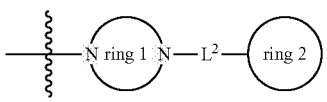

For inhibiting growth of CQ-susceptible microorganisms, including malaria parasites (e.g. *Plasmodium*), as well as other $CQ^S$ or $CQ^R$ microorganisms:

1) if $L^1$ is $C_2$ alkylene and $L^2$ is $C_2$ alkylene and ring 1 is

then ring 2 is not 3-diethylamino-4-hydroxy-phenyl;

2) if $L^1$ is $C_2$ alkylene and $L^2$ is a bond and ring 1 is

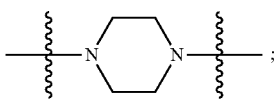

then ring 2 is not a phenyl ring substituted with oxazolidonyl;

3) if $L^1$ is $C_3$ alkylene and $L^2$ is $C_3$ alkylene and ring 1 is

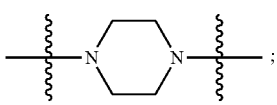

then ring 2 is not pyrrolidyl, piperidyl, or azepanyl;

4) if $L^1$ is $C_2$ alkylene and $L^2$ is $C_3$ or $C_7$ alkylene and ring 1 is

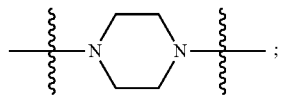

then ring 2 is not substituted piperidyl;

5) if $L^1$ is $C_3$ alkylene and $L^2$ is $C_3$ or $C_6$ alkylene and ring 1 is

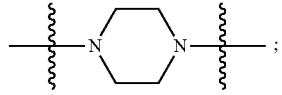

then ring 2 is not substituted piperidyl;

Embodiments of the invention are also directed to a method of inhibiting growth of a CQ-susceptible microorganism, the method comprising contacting at least one CQ-susceptible microorganism with a growth-inhibiting amount (e.g., growth inhibiting amount) of a compound of formula I or salt or solvate or stereoisomer thereof. In some embodiments, the CQ-susceptible microorganism is a *Plasmodium* parasite.

In embodiments of the invention, a method of inhibiting home detoxification in a CQ-susceptible microorganism is provided, the method comprising contacting at least one CQ-susceptible microorganism with a compound of formula I or salt or solvate or stereoisomer thereof. In some embodiments, the CQ-susceptible microorganism is a *Plasmodium* parasite.

Embodiments of the invention are also directed to a method of inhibiting or treating diseases or conditions caused by a CQ-susceptible microorganism such as malaria in a subject, the method comprising administering to the subject a therapeutically effective amount of a compound of formula I or salt or solvate or stereoisomer thereof.

Since the compounds can inhibit growth of CQ-susceptible microorganisms, such compounds are also useful as research tools. Accordingly, embodiments of the invention also include the provision of a method for using a compound of formula I or a salt or solvate or stereoisomer thereof as a research tool for studying a biological system or sample, or for discovering new chemical compounds that can inhibit the growth of a CQ-susceptible microorganism.

Embodiments of the invention are also directed to processes and novel intermediates useful for preparing compounds of formula I or a salt or solvate or stereoisomer thereof. Accordingly, embodiments of the invention include the provision of a process of preparing a compound of formula I, the process comprising: contacting a compound of formula

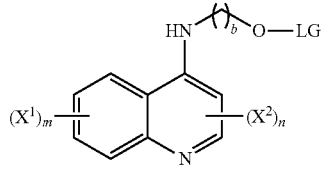

with a compound of formula

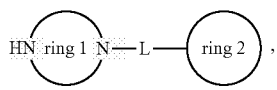

wherein O-LG represents an activated leaving group, L is $L^2$ or $L^3$, and other parameters are defined herein.

Embodiments of the invention are also directed to a compound of formula I or a salt or solvate or stereoisomer thereof, for use in therapy or as a medicament.

Additionally, embodiments of the invention are directed to the use of a compound of formula I or a salt or solvate or stereoisomer thereof, for the manufacture of a medicament; especially for the manufacture of a medicament for the treatment of diseases or conditions caused by a CQ-susceptible microorganism.

Characterization of MCQ Functional Properties

The disclosed MCQ compounds are useful, at least, in the treatment of a disease or condition caused by a CQ-susceptible microorganism, such as malaria or *Plasmodium* infection. Without being bound by theory, CQ is believed to exert its inhibitory effect on *Plasmodium* parasites by binding heme in the DV of the parasite. Accordingly, if it is desirable to do so, non-limiting methods useful to functionally characterize MCQ compounds are heme binding assays and in vitro and in vivo *Plasmodium* bioassays.

1. Heme Binding

Optionally, heme binding of MCQ compounds can be determined by any method known in the art, including, for example, spectrophotometric methods, like UV-VIS spectroscopy or NMR spectroscopy. Methods of measuring heme binding to a variety of molecules using the UV-VIS spectrum have been described (see, e.g., Xu et al. 2001. *J. Inorg. Biochem.* 86(2-3):617-625; Xu et al. 2002. *Antimicrob. Agents Chemother,* 46(1):144-150, each of the foregoing which is incorporated herein by reference in its entirety). Generally, a heme-binding compound (such as a disclosed MCQ) is mixed in increasing concentration with heme (or a heme model compound, such as porphyrin or metalloporphyrin), and the absorbance spectrum is measured from the ultraviolet region well into the visible region (from about 300 nm to about 750 nm). This spectral range includes the so-called Soret and Q-band regions that arise from porphyrin or metalloporphyrin absorbance. Upon interaction between a heme-binding compound and heme (or a heme model compound, such as porphyrin or metalloporphyrin), decreased absorbance in the Soret region is observed. Without being bound by theory, it is believed that such decrease arises from pi-pi stacking interactions (White, Aggregation of porphyrins and metalloporphyrins, In: The Porphyrins. ed. by Dolphin, NewYork: Academic Press, 1978, pp. 303-339).

The formation of heme-MCQ complexes can be determined by UV-VIS spectrophotometric titration, using a variety of commercially available spectrophotometers (such as a Varian-Cary 3E spectrophotometer). The approximate pH of the plasmodial DV, where CQ (or MCQ) is believed to bind to heme in vivo, is pH 4.7; thus, it is useful (though not obligatory) to conduct heme-binding reactions at a pH (e.g., 4.7 or 7) and temperature (e.g., 25° C.) similar to DV conditions in vivo. Titrations of heme (or a heme model) with a MCQ compound can be performed, for example, by successive addition of aliquots of a 1 mM MCQ solution to a 10 μM heme solution. Optionally, pH can be monitored throughout the procedure to ensure that it remains unchanged. In some circumstances, UV-VIS spectral data can be analyzed digitally, and absorbance readings and concentrations corrected for dilution effects. The amount of heme-MCQ complex versus amount of MCQ added to the reaction can be plotted. Such titration curves can be analyzed with Hill plot and non-linear curve fitting methods as described previously (Xu et al. 2002. *Antimicrob. Agents Chemother.* 46(1):144-150) to obtain association constants for the heme-MCQ binding reaction.

NMR is another optional method that can be used, for example, to provide information about stoichiometry, interaction affinities, and structural details of complexes between MCQ molecules and heme (or heme models, such porphyrins or metalloporphyrins) (White. Aggregation of porphyrins and metalloporphyrins, In: The Porphyrins. ed. by Dolphin, NewYork: Academic Press, 1978, pp. 303-339).

NMR parameters useful to measure include changes in chemical shift, line-width, and relaxation times. For example, NNM relaxation times give information about proximity to paramagnetic centers (e.g., the Fe in heme), or chemical exchange between species (e.g., bound and free MCQ). A fourth useful parameter to measure is peak area ratio, which is convenient if exchange between complexes is unexpectedly slow. NMR studies can be performed by adding aliquots of heme to MCQ solutions, then monitoring chemical shifts, linewidths, and relaxation times of the MCQ NMR signals. Such techniques are well known in the art (see, for instance, Xu et al. 2001. *J. Inorg. Biochem.* 86(2-3):617-625).

If desirable, fluorescence confocal microscopy can also be used to determine whether an MCQ is localized to the DV (see, for instance, Xu et al. 2002. *Mol. Biochem. Parasitol.* 123(1):47-54, which is incorporated herein by reference in its entirety).

2. In Vitro and In Vivo Bioassays

One exemplary method for measuring inhibitory effects of MCQ compound in vitro has been reported by Smilkstein et al. (2004. *Antimicrob. Agents Chemother.* 48(5):1803-1806, which is incorporated herein by reference in its entirety). This method employs fluorescent detection of the level of parasitemia in cultured red blood cells and can be automated for high-throughput screening of antimalarial RCQs. This exemplary method allows the inhibitory agent (such as a MCQ) to be in contact with the parasite for an entire developmental cycle without purine starvation, which is in contrast to the traditional $^3$H-hypoxanthine method (Desjardins et al. 1979. *Antimicrob. Agents Chemother.* 16(6):710-718, which is incorporated herein by reference in its entirety). Briefly, to perform the Smilkstein et al. method, an initial parasitemia of approximately 0.2% is attained by adding uninfected red blood cells (RBCs) to a stock culture of *Plasmodium*-infected RBCs. Infected cells (2% v/v) are combined with RCQs (for example, dissolved in DMSO), e.g., at a final concentration of $10^{-1}$ to $10^{-4}$ M. Chloroquine can be added (instead of a MCQ) to some infected RBCs as a control. After a period of incubation (such as about 72 hours), a sufficient amount (e.g., 100 μL) of a fluorescent DNA binding dye-detergent mixture (e.g., Sybr Green I dye-detergent mixture) to lyse cells and bind to DNA is added to the reactions. Because uninfected RBCs have no DNA, only parasite DNA (in infected RBCs) is available for binding to the fluorescent dye (e.g., Sybr Green I). Samples are then incubated in the dark for a period of time (e.g., one hour), followed by measurement of levels of fluorescence. For Sybr Green 1, excitation and emission wavelength are 485 and 530 nm, respectively. Fluorescence readings, which represent the amount of parasite DNA in the sample, can be plotted against the Log [drug] and fit to a curve by nonlinear regression to obtain the $IC_{50}$ value for the tested compound.

Various *Plasmodium* parasites are available for testing in vitro efficacy of antimalarial compounds (such as a disclosed MCQ). The disclosed MCQ can be effective against $CQ^R$ and/or $CQ^S$ *Plasmodium* strains (such as $CQ^R$ and $CQ^S$ *P. falciparum* strains). Exemplary $CQ^S$ and $CQ^R$ *P. falciparum* strains are shown in the following table;

TABLE 2

Drug Susceptibility of *P. falciparum* strain

| Drug | \multicolumn{7}{c}{*P. falciparum* strain} |
|---|---|---|---|---|---|---|---|
| | D6 | FCR3 | W2 | Dd2 | 3D7 | TM91C235 | 7G8 |
| CQ | S | R | R | R | S | R | R |
| Quinine | S | S | R | R | NC | R | |
| Mefloquine | S/R | S | S | R | NC | R | |
| Pyrimethamine | S | S | R | R | NC | R | |
| Cycloguanil | S | S | R | S | NC | NC | |
| Sulfadoxine | S | S | R | S | NC | R | |

S = sensitive; R = resistant; S/R = intermediate level of resistance; NC = not characterized Antimalarial compounds can also be tested for efficacy in vivo. One non-limiting exemplary method for performing such testing is the 4-day suppressive test (Peters. 1975. *Ann. Trop. Med. Parasitol.* 69(2):155-171, which is incorporated herein by reference in its entirety). Briefly, such test involves collecting *P. chabaudi* (Mackinnon and Read. 2004. *Philos. Trans. R. Soc. Lond. B Biol. Sci.* 359:965-986; Mackinnon et al. 2002. *Exp. Parasitol.* 101(2-3):121-128, each of which is incorporated herein by reference in its entirety) from a donor animal harboring about 20% parasitemia. Male CF-1 mice at 4-5 weeks of age (about 20 g) are infected with about $10^7$ infected red blood cells via 100 μL tail vein injection and randomly sorted into groups of 4 mice each on Day 0. One hour after infection, the mice receive the test agent via oral gavage, or by the intraperitoneal route (at approximately 1-10 times the in vitro $IC_{50}$ values). Drugs are administered once daily for at least 4 days beginning at Day 0. Animals are tested weekly for levels of parasitemia, for example, by microscopic analysis of Giemsa-stained blood smears. Efficacy of a tested compound in this bioassay is measured by inhibition of parasite growth as defined previously. In some examples, subjects are expected to be freed of measurable parasites after a period of treatment (such as 30 days).

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

A representative synthesis for compounds of formula I is shown in FIG. 1. In FIG. 1, with parameters defined herein, Compound 100 is reacted with Compound 101 to give Compound 102. In Compound 100, $X^{10}$ is a leaving group. Examples of suitable leaving groups include, but are not limited to, halogen, mesylate, tosylate, or triflate. In Compound 101, b is an integer from 1 to 12, thus forming an alkylene chain. The alkylene chain can be optionally substituted according to the disclosure herein. Compound 100 and 101 react in a nucleophilic substitution reaction to give Compound 102. The nucleophilic substitution reaction can be run neatly or with a suitable solvent. The nucleophilic reaction can be run at various temperatures, including with cooling, at room temperature, or with heating. One skilled in the art would be able to determine suitable reaction conditions according to the specific reactants.

The hydroxyl group of Compound 102 is then converted to an activated leaving group to give Compound 103. In Compound 103, —O-LG represents an activated leaving group. The carbon atom attached to an activated leaving group is susceptible to nucleophilic attack or readily eliminates. Conversion of the hydroxyl group to an activated leaving group can be performed by various methods. In certain methods, the hydroxyl group is converted to an alkyl sulfonate or aryl sulfonate, such as mesylate, tosylate, and triflate.

The activated leaving group of Compound 103 is reacted with a nucleophilic amino group of Compound 104 to give Compound 105 through a nucleophilic substitution reaction. In Compound 103, —O-LG is a leaving group. Examples of suitable leaving groups include, but not limited to, mesylate, tosylate, or triflate. In Compound 104, L is an alkylene or substituted alkylene chain, such as $L^2$ or $L^3$, as defined herein. The alkylene chain can be optionally substituted according to the disclosure herein. Compound 103 and 104 react in a nucleophilic substitution reaction to give Compound 105. The nucleophilic substitution reaction can be run neatly or with a suitable solvent. The nucleophilic reaction can be run at various temperatures, including with cooling, at room temperature, or with heating. One skilled in the art would be able to determine suitable reaction conditions according to the specific reactants.

The secondary amine on Compound 105 can be derivatized to form Compound 106 with $R^1$ group. Examples of further derivatization of Compound 105 to provide Compound 106 include, but are not limited to: the amine can be reacted with aldehydes or ketones in the presence of a reducing agent such as sodium triacetoxyborohydride to reductively alkylate the amine; with acid chlorides or carboxylic acids and an amide bond forming reagent to form amides; and with sulfonyl chlorides to form sulfonamides.

Pharmaceutical Compositions

The disclosed MCQ compounds are useful for the inhibition and treatment of diseases or conditions caused by a CQ-susceptible microorganism. The disclosed MCQ compounds are useful for the treatment of malaria and/or inhibiting the growth of malarial parasites, such as *P. falciparum*. Accordingly, pharmaceutical compositions comprising at least one disclosed MCQ compound are also described herein.

A pharmaceutical composition comprising an MCQ compound can be administered to a subject alone, or in combination with other supplementary active agents. The pharmaceutical compositions can be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A subject MCQ compound can be administered to a subject using any convenient means capable of resulting in the desired reduction in disease condition or symptom. Thus, a subject MCQ compound can be incorporated into a variety of formulations for therapeutic administration. More particularly, a subject MCQ compound can be formulated into pharmaceutical compositions by combination with appropriate pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols.

Formulations for pharmaceutical compositions are well known in the art. For example, Remington's Pharmaceutical Sciences, by E. W. Martin, Mack Publishing Co., Easton, Pa., 15th Edition, 1975, describes exemplary formulations (and components thereof) suitable for pharmaceutical delivery of disclosed MCQ compounds. Pharmaceutical compositions comprising at least one of the disclosed MCQ compounds can be formulated for use in human or veterinary medicine. Particular formulations of a disclosed pharmaceutical composition can depend, for example, on the mode of administration (e.g., oral or parenteral) and/or on the location of the infection to be treated (e.g., liver-stage and/or blood-stage malaria parasites). In some embodiments, formulations include a pharmaceutically acceptable carrier in addition to at least one active ingredient, such as a MCQ compound. In other embodiments, other medicinal or pharmaceutical agents, for example, with similar, related or complementary effects on the affliction being treated (such as malaria or *Plasmodium* infection), can also be included as active ingredients in a pharmaceutical composition.

Pharmaceutically acceptable carriers useful for the disclosed methods and compositions are conventional in the art. The nature of a pharmaceutical carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) buffered solutions; (21) polyesters, polycarbonates and/or polyanhydrides; and (22) other non-toxic compatible substances employed in pharmaceutical formulations.

The disclosed pharmaceutical compositions can be formulated as a pharmaceutically acceptable salt of a disclosed MCQ compound. Pharmaceutically acceptable salts are non-toxic salts of a free base form of a compound that possesses the desired pharmacological activity of the free base. These salts can be derived from inorganic or organic acids. Non-limiting examples of suitable inorganic acids are hydrochloric acid, nitric acid, hydrobromic acid, sulfuric acid, hydriodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, methyl sulfonic acid, salicylic acid, formic acid, trichloroacetic acid, trifluoroacetic acid, gluconic acid, asparagic acid, aspartic acid, benzenesulfonic acid, p-toluenesulfonic acid, naphthalenesulfonic acid, and the like. Lists of other suitable pharmaceutically acceptable salts are found in Remington's Pharmaceutical Sciences, 17th Edition, Mack Publishing Company, Easton, Pa., 1985. A pharmaceutically acceptable salt can also serve to adjust the osmotic pressure of the composition.

An MCQ compound can be used alone or in combination with appropriate additives to provide oral formulations, which may be in any suitable form (e.g., liquid formulations, tablets, powders, granules or capsules, and the like). Tablets, powders, granules or capsules can be produced, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An MCQ compound can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation can also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

Certain embodiments of the pharmaceutical compositions comprising a disclosed MCQ compound can be formulated in unit dosage form suitable for individual administration of precise dosages. The amount of active ingredient (e.g., MCQ compound) administered will depend on the subject being treated, the severity of the affliction, and the manner of administration, and is known to those skilled in the art. Within these bounds, the formulation to be administered will contain a quantity of the extracts or compounds disclosed herein in an amount effective to achieve the desired effect in the subject being treated.

In some embodiments, at least one modified chloroquine (MCQ) compound, or a salt, solvate or stereoisomer thereof, is present in the pharmaceutical composition in an amount ranging from about 0.5 percent to about 90 percent by weight of the pharmaceutical composition. In some embodiments, the at least one MCQ compound is present in the pharmaceutical composition in an amount ranging from about 1 percent to about 85 percent by weight of the pharmaceutical composition. In some embodiments, the at least one MCQ compound is present in the pharmaceutical composition in an amount ranging from about 5 percent to about 80 percent by weight of the pharmaceutical composition. In some embodiments, the at least one MCQ compound is present in the pharmaceutical composition in an amount ranging from about 10 percent to about 75 percent by weight of the pharmaceutical composition. In some embodiments, the at least one MCQ compound is present in the pharmaceutical composition in an amount ranging from about 15 percent to about 50 percent by weight of the pharmaceutical composition. In some embodiments, the at least one MCQ compound is present in the pharmaceutical composition in an amount ranging from about 25 percent to about 35 percent by weight of the pharmaceutical composition.

In some embodiments, the at least one MCQ compound is present in the pharmaceutical composition in an amount ranging from about 2 percent to about 25 percent by weight of the pharmaceutical composition. In some embodiments, the at least one MCQ compound is present in the pharmaceutical composition in an amount ranging from about 2 percent to about 20 percent by weight of the pharmaceutical composition. In some embodiments, the at least one MCQ compound is present in the pharmaceutical composition in an amount ranging from about 2 percent to about 10 percent by weight of the pharmaceutical composition.

In some embodiments, the at least one MCQ compound is present in the pharmaceutical composition in an amount ranging from about 5 percent to about 15 percent by weight of the pharmaceutical composition. In some embodiments, the at least one MCQ compound is present in the pharmaceutical composition in an amount ranging from about 5 percent to about 10 percent by weight of the pharmaceutical composition.

In some embodiments, the at least one MCQ compound is present in the pharmaceutical composition in an amount greater than about 20 percent by weight of the pharmaceutical composition. In some embodiments, the at least one MCQ compound is present in the pharmaceutical composition in an amount greater than about 30 percent by weight of the pharmaceutical composition. In some embodiments, the at least one MCQ compound is present in the pharmaceutical composition in an amount greater than about 35 percent by weight of the pharmaceutical composition. In some embodiments, the at least one MCQ compound is present in the pharmaceutical composition in an amount greater than about 40 percent by weight of the pharmaceutical composition.

In some embodiments, the pharmaceutical composition is a solution.

In some embodiments, the pharmaceutical composition is injectable.

In some embodiments, the pharmaceutical composition can be administered parenterally.

In some embodiments, the pharmaceutical composition can be administered subcutaneously.

In some embodiments, the pharmaceutical composition can be administered intravenously.

In some embodiments, the pharmaceutical composition can be administered orally.

The pharmaceutical composition can further comprise one or more pharmaceutically acceptable excipients. Suitable pharmaceutically acceptable excipients include, but are not limited to, sweeteners, flavoring agents, preservatives, and coloring agents. Such excipients are known in the art. Examples of suitable pharmaceutical excipients are described in Remington's Pharmaceutical Sciences at pages 1447-1676 (Alfonso R. Gennaro ed., 19$^{th}$ ed. 1995), which is incorporated herein by reference in its entirety.

The pharmaceutical composition can further comprise one or more pharmaceutically acceptable preservatives. Examples of preservatives include, but are not limited to, potassium sorbate, methylparaben, propylparaben, benzoic acid and its salts, esters of parahydroxybenzoic acid such as butylparaben, alcohols such as ethyl or benzyl alcohol, phenolic compounds such as phenol, and quaternary ammonium compounds such as benzalkonium chloride.

In some embodiments, a subject MCQ compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject MCQ compound can be utilized in aerosol formulation to be administered via inhalation. A subject MCQ compound can be formulated into pressurized acceptable propellants such as dichlorodifluoromethane, propane, nitrogen and the like.

Furthermore, a subject MCQ compound can be made into suppositories by mixing with a variety of bases such as emulsifying bases or water-soluble bases. A subject MCQ compound can be administered rectally via a suppository. The suppository can include vehicles such as cocoa butter, carbowaxes and polyethylene glycols, which melt at body temperature, yet are solidified at room temperature.

The term "unit dosage form," as used herein, refers to physically discrete units suitable as unitary dosages for human and animal subjects, each unit containing a predetermined quantity of an MCQ compound calculated in an amount sufficient to produce the desired effect in association with a pharmaceutically acceptable diluent, carrier or vehicle. The specifications for a subject MCQ compound depend on the particular compound employed and the effect to be achieved, and the pharmacodynamics associated with each compound in the host.

The dosage form of a disclosed pharmaceutical composition will be determined by the mode of administration chosen. For example, in addition to injectable fluids, topical or oral dosage forms can be employed. Topical preparations can include eye drops, ointments, sprays and the like. Oral formulations can be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions comprising a disclosed MCQ compound can be formulated in unit dosage form suitable for individual administration of precise dosages. The amount of such a MCQ compound administered will depend on the subject being treated, the severity of the affliction, and the manner of administration, and is known to those skilled in the art. Within these bounds, the formulation to be administered will contain a quantity of the compounds disclosed herein in an amount effective to achieve the desired effect in the subject being treated.

Methods of Use

The present disclosure includes methods of inhibiting or treating a disease or condition caused by a CQ-susceptible microorganism. CQ-susceptible microorganisms are microorganisms which exhibit reduced growth in the presence of CQ. CQ-susceptible microorganisms can include microorganisms classified as CQ sensitive or CQ resistant. "CQ sensitive" (or "CQS") and "CQ resistant" (or "CQR") as used herein generally refer to the relative susceptibility of microorganism strains to growth inhibition by CQ. Thus "CQR microorganisms" can exhibit CQ-mediated growth inhibition, but require a higher dose than required for a similar level of growth inhibition of a CQ sensitive strain of the same microorganism.

Methods of assessing the effect of CQ on growth of a microorganism can be accomplished using methods well known in the art. For example, CQ-susceptibility of a microorganism can be assessed by comparing growth of the microorganism in the presence and absence of CQ wherein the microorganism tested is cultured under suitable conditions or is present in an animal model. Susceptibility of a microorganism to treatment using a compound of the present disclosure can also be assessed by comparing growth of the microorganism in the presence and absence of one or more compounds of the present disclosure wherein the microorganism tested is cultured under suitable conditions or is present in an animal model. Exemplary CQ-susceptible microorganisms include those that exhibit reduced growth in the presence of up to 100 µM chloroquine. In certain cases, CQ-susceptible microorganisms are those that exhibit reduced growth in the presence of up to 50 µM chloroquine exhibit reduced growth in the presence of CQ in the nM range or in the pM range.

In certain cases, the CQ-susceptible microorganism is a *Plasmodium* parasite such as a CQR or CQS strain. CQ-susceptible microorganisms include microorganisms in which CQ reduces the ability of the microorganism to detoxify heme detoxification and/or which facilitate growth inhibition by increasing pH of organelles of the microorganism.

Embodiments of the invention relate to methods of treating malaria and/or inhibiting *Plasmodium* parasite growth (including $CQ^R$ and $CQ^S$ parasites). Examples of pathogens whose growth can be inhibited include, but are not limited to, *P. falciparum, P. vivax, P. ovate, P. malariae*, including combinations thereof. In other examples, the disease or *Plasmodium* parasite to be treated is resistant to CQ or other traditional malaria treatment.

Disclosed methods includes administering a disclosed MCQ compound (and, optionally, one or more other pharmaceutical agents) to a subject in a pharmaceutically acceptable carrier and in an amount effective to inhibit or treat a disease or condition caused by a CQ-susceptible microorganism. The treatment can be used prophylactically in any subject in a demographic group at substantial risk for such diseases; for example, subjects who are traveling to areas where malaria (such as $CQ^R$ malaria) is endemic (including, e.g., Southeast Asia, Africa, Papua New Guinea, Indonesia, Thailand, and India). Notably, pregnant women are twice as likely to attract malaria-carrying mosquitoes as non-pregnant women (perhaps due to a greater volume of exhaled air and a warmer skin surface), and, therefore, are especially vulnerable to malaria. Alternatively, subjects can be selected using more specific criteria, such as a probable or definitive diagnosis of malaria or *Plasmodium* infection based on, for example, clinical signs and symptoms and/or laboratory evidence of parasite infection. An example of such a subject is a person who presents clinically with symptoms resembling the flu (including periods of chills and fever lasting several hours and occurring every few days). In more severe cases, an infected subject can present with enlarged spleen and/or liver, anemia, and jaundice. Other subjects can be identified based on positive tests for parasite-specific proteins, including plasmodial histidine rich protein-2 (HRP-2) or parasite-specific lactate dehydrogenase (PLDH) or parasite DNA. A number of antibodies specific for *Plasmodium* parasites are available and are useful for diagnostic immunoassays or immunofluorescence techniques. PCR can also be used to diagnosis malaria in a subject (Am. J. Trap. Med. Hyg., 65(4):355-363, 2001).

In some embodiments, the MCQ compound, or a pharmaceutical composition containing the same, is administered to a subject in which a disease or condition has developed, wherein the disease or condition is caused by a microorganism formerly susceptible but currently resistant to chloroquine. In such embodiments, the MCQ compound, or pharmaceutical composition containing the same, is used to treat the disease or condition in which chloroquine has been found to be less effective or not effective. In some embodiments, chloroquine is about 10-fold less effective than the MCQ compound. In some embodiments, chloroquine is about 20-fold less effective than the MCQ compound. In some embodiments, chloroquine is about 25-fold, 50-fold, 100-fold or more less effective than the MCQ compound.

Disclosed methods also includes administering a disclosed MCQ compound to a subject in need thereof in a pharmaceutically acceptable carrier to inhibit or treat diseases or conditions caused by a CQ-susceptible microorganism.

Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a MCQ will depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (host) being treated. For example, this can be the amount of a MCQ necessary to prevent, inhibit, reduce or relieve a disease or condition caused by a CQ-susceptible microorganism, such as a *Plasmodium* infection or malaria. Ideally, a therapeutically effective amount of a MCQ is an amount sufficient to prevent, inhibit, reduce or relieve a disease or condition caused by a CQ-susceptible microorganism without causing a substantial cytotoxic effect on host cells. It is believed that disclosed MCQs will be well tolerated in human subjects because, at least some, quinoline analogs (such as CQ) have been demonstrated safe for administration to human subjects in therapies.

Therapeutically effective doses (growth inhibitory amounts) of a disclosed MCQ compound or pharmaceutical composition can be determined by one of skill in the art, with a goal of achieving local (e.g., tissue) concentrations that are at least as high as the $IC_{50}$ of the applicable compound disclosed in the examples herein. The effective amount administered to the subject depends on a variety of factors including, but not limited to the age, body weight, general health, sex and diet of the subject being treated, the condition being treated, the severity of the condition, the activity of the specific MCQ compound being administered, the metabolic stability and length of action of that compound, mode and time of administration, rate of excretion and the drug combination. The amount of the pharmaceutical composition that is effective in the treatment or prevention of a condition, such as malaria, can be determined by standard clinical techniques well known to those of skill in the art. In addition, in vitro or in vivo assays can optionally be employed to help identify optimal dosage ranges. One of ordinary skill in the art will readily be able to determine the precise dose to be employed. Suitable effective dosage amounts, however, typically range from about 0.1 mg/kg of body weight to about 250 mg/kg of body weight, from about 0.25 mg/kg of body weight to about 200 mg/kg of body weight, from about 0.5 mg/kg of body weight to about 100 mg/kg of body weight, from about 0.75 mg/kg of body weight to about 50 mg/kg of body weight, or from about 1 mg/kg of body weight to about 25 mg/kg of body weight. The effective dosage amounts described herein refer to total amount of MCQ compound administered. For example, if more than one MCQ compound is administered, the effective dosage amounts correspond to the total amount of MCQ compound administered.

An example of a dosage range is from about 0.1 to about 250 mg/kg body weight administered orally in single or divided doses. In particular examples, an oral dosage range is from about 1.0 to about 100 mg/kg body weight administered orally in single or divided doses, including from about 1.0 to about 50 mg/kg body weight, from about 1.0 to about 25 mg/kg body weight, from about 1.0 to about 10 mg/kg body weight (assuming an average body weight of approximately 70 kg; values adjusted accordingly for persons weighing more or less than average). For oral administration, the compositions are, for example, provided in the form of a tablet containing from about 50 to about 1000 mg of the active ingredient, particularly about 75 mg, about 100 mg, about 200 mg, about 400 mg, about 500 mg, about 600 mg, about 750 mg, or about 1000 mg of the active ingredient for the symptomatic adjustment of the dosage to the subject being treated. In one exemplary oral dosage regimen, a tablet containing from about 500 mg to about 1000 mg active ingredient is administered once (e.g., a loading dose) followed by administration of ½ dosage tablets (e.g., from about 250 to about 500 mg) each 6 to 24 hours for at least 3 days.

In some embodiments, the pharmaceutical composition can be administered parenterally. In some embodiments, the pharmaceutical composition can be administered subcutaneously. In some embodiments, the pharmaceutical composition can be administered intravenously, in some embodiments, the pharmaceutical composition can be administered orally.

In some embodiments, the pharmaceutical composition can be administered by injection, which includes, but is not limited to, the following means of delivery: intradermal; intramuscular; intraperitoneal; intravenous; and subcutaneous.

In practicing the subject methods, a subject can be administered a single dose or two or more doses over a given period of time. For example, over a given treatment period of one month, 1 or more doses, such as 2 or more doses, 3 or more doses, 4 or more doses, 5 or more doses, etc., can be administered to the subject, where the doses can be administered weekly or daily or even multiple times per day.

The specific dose level and frequency of dosage for any particular subject can be varied and will depend upon a variety of factors, including the activity of the specific MCQ compound, the metabolic stability and length of action of that compound, the age, body weight, general health, sex and diet of the subject, mode and time of administration, rate of excretion, drug combination, and severity of the condition of the host undergoing therapy.

In some embodiments, the effective amount of the pharmaceutical composition is administered once per day until 2-3 days after cessation of the condition.

In some embodiments, the effective amount of the pharmaceutical composition is administered as two doses per day until 2-3 days after cessation of the condition.

In some embodiments, the effective amount of the pharmaceutical composition is administered once per day for from about 1 to about 10 days. For example, the effective amount of the pharmaceutical composition can be administered once per day for about 1, 2, 3, 4, 5, 6, 7, 8, 9, or 10 days.

In some embodiments, the effective amount of the pharmaceutical composition is administered as two doses per day for from about 1 to about 10 days. For example, the effective amount of the pharmaceutical composition can be administered as two doses per day for about 1, 2, 3, 4, 5, 6, 7, 8, 9, or 10 days.

In some embodiments, the effective amount of the pharmaceutical composition is administered once per day for about 14 days.

In some embodiments, the effective amount of the pharmaceutical composition is administered as two doses per day for about 14 days.

In some embodiments, the effective amount of the pharmaceutical composition is administered once per day for about 21 days.

In some embodiments, the effective amount of the pharmaceutical composition is administered as two doses per day for about 21 days.

In some embodiments, to treat some conditions, the pharmaceutical compositions of the invention can be administered for even longer periods of time, for example several months.

Embodiments of the invention also relate to combinations of one or more disclosed MCQs with one or more other agents or therapies useful in the treatment of malaria and/or *Plasmodium* parasitemia. For example, one or more disclosed MCQs can be administered in combination with effective doses of other medicinal and pharmaceutical agents, or in combination other non-medicinal therapies, such as hormone or radiation therapy. The term "administration in combination with" refers to both concurrent and sequential administration of the active agents. In some examples, the one or more other antimalarial agents or therapies can include artesunate and mefloquine (either individually or in an artesunate-mefloquine combination), or sulfadoxine and pyrimethamine (either individually or in a sulfadoxine-pyrimethamine combination (commercially available as Fanisdar™)). In particular examples, the one or more other antimalarial agents or therapies have at least one different mode of action than is proposed (although not binding) for a disclosed MCQ; thus, for instance, a combination agent or therapy can target mitochondria and/or dihydrofolate reductase. In another example, two or more MCQs could be administered together.

Furthermore, the effective dosage amounts described herein refer to total amount of MCQ compound administered. For example, if more than one MCQ compound is administered, the effective dosage amounts correspond to the total amount of MCQ compound administered.

Other method embodiments involve inhibiting the growth of at least one *Plasmodium* (such as *P. falciparum, P. vivax, P. ovale*, or *P. malariae*, or a combination thereof) by contacting the parasite(s) with a growth inhibitory amount of a disclosed MCQ. Contact between a MCQ and a parasite may occur in vitro (such as in culture conditions or treatment of blood ex vivo) or in vivo (such as in a subject infected with at least one *Plasmodium*). A growth inhibitory amount is from about 1 nM to about 1 µM of a disclosed MCQ (such as from about 5 nM to about 50 nM, or from about 5 nM to about 25 nM).

Research Applications

Since the compounds can inhibit growth of CQ-susceptible microorganisms, such compounds are also useful as research tools. Accordingly, embodiments of the invention are directed to a method for using a compound of formula I or a salt or solvate or stereoisomer thereof as a research tool for studying a biological system or sample, or for discovering new chemical compounds that can inhibit the growth of a CQ-susceptible microorganism.

In some embodiments, a method of studying a biological system or sample known to comprise a CQ-susceptible microorganism is provided, the method comprising: (a) contacting the biological system or sample with a compound of formula I or a salt or solvate or stereoisomer thereof; and (b) determining the inhibiting effects caused by the compound on the biological system or sample.

Any suitable biological system or sample having a CQ-susceptible microorganism can be employed in such studies which can be conducted either in vitro or in vivo. Representative biological systems or samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

In some embodiments, the subject compounds are provided as additives for storage of blood and blood products. Blood products include whole blood, red blood cells, white blood cells, platelets, serum and plasma. The amount of subject compound added to the blood or blood product is an effective amount to inhibit growth of a CQ-susceptible microorganism.

When used as a research tool, a biological system or sample comprising a CQ-susceptible microorganism is typically contacted with an inhibiting amount of a subject compound. After the biological system or sample is exposed to the compound, the effects of inhibition of a CQ-susceptible microorganism are determined using conventional procedures and equipment, such as by home binding assay or in vitro and in vivo bioassays. Exposure encompasses contacting the biological system or sample with the compound or administering the compound to a subject. The determining step can involve measuring a response (a quantitative analysis) or can involve making an observation (a qualitative analysis). Measuring a response involves, for example, determining the effects of the compound on the biological system or sample using conventional procedures and equipment, such as radioligand binding assays and measuring ligand-mediated changes in functional assays. The assay results can be used to determine the activity level as well as the amount of compound necessary to achieve the desired result, that is, a CQ-susceptible microorganism-inhibiting amount.

Additionally, the subject compounds can be used as research tools for evaluating other chemical compounds, and thus are also useful in screening assays to discover, for example, new compounds having a CQ-susceptible microorganism-inhibiting activity. In this manner, a subject compound is used as a standard in an assay to allow comparison of the results obtained with a test compound and with the subject compounds to identify those test compounds that have about equal or superior activity, if any. For example, $IC_{50}$ data for a test compound or a group of test compounds is compared to the $IC_{50}$ data for a subject compound to identify those test compounds that have the desired properties, for example, test compounds having an $IC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; wherein step (a) is conducted either before, after or concurrently with step (b); and (c) comparing the first assay value from step (a) with the second assay value from step (b) to generate comparison data. The biological assay can be selected from CQ-susceptible microorganism-inhibition, *Plasmodium*-inhibition, cytotoxicity, and bioavailability. An exemplary biological assay includes a fluorescence assay for determining $IC_{50}$ of antimalarial drugs, such as using CQ-susceptible microorganism or *Plasmodium*.

Having described the invention in detail, it will be apparent that modifications, variations, and equivalent embodiments are possible without departing from the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Synthesis of 7-chloro-n-(3-(4-(4-methoxyphenyl) piperazin-1-yl)propyl)quinolin-4-amine Preparation 1: Synthesis of 3-(7-chloroquinolin-4-ylamino)propan-1-ol (Prep 1)

A mixture of 4,7-dichloroquinoline (25.35 g, 0.128 mol) and 3-aminopropanol (120 mL, 1.57 mol) were heated with stirring at 130-140° C. for 24 hours. After cooling, the reaction mixture was poured into water (500 mL) and filtered, and the solid residue was dried then boiled in ethyl acetate (250 mL) to give the title compound (27.3 g, 90%) as an off-white solid.

Preparation 2: Synthesis of 3-(7-chloroquinolin-4-ylamino)propyl methanesulfonate (Prep 2

To a suspension of product of Preparation 1 (0.5 g, 2.1 mmol) in anhydrous THF (10 mL) under a nitrogen atmosphere was added triethylamine (0.66 mL, 4.2 mmol). The mixture was cooled to below 0° C. Methanesulfonyl chloride (0.17 mL, 2.2 mmol) was added slowly, keeping the temperature below 5° C., and the reaction mixture was stirred in an ice bath for 45 min. After dilution with saturated $NaHCO_3$ solution (20 mL), the reaction mixture was extracted with ether (20 mL then 2×10 mL). The organic extracts were dried over $MgSO_4$, filtered, and evaporated to leave the title compound (0.42 g, 63%) as a white solid.

Preparation 3: Synthesis of 7-chloro-N-(3-(4-(4-methoxyphenyl)piperazin-1-yl)propyl)quinolin-4-amine (Prep 3)

The product of Preparation 2 (0.69 g, 0.00219 mol) and 1-(4-methoxyphenyl)piperazine (0.51 g, 0.00263 mol) were dissolved in THF (15 mL) and triethylamine (0.44 g, 0.00438 mol) was added. The reaction mixture was stirred and heated at reflux for 4 days. After cooling to room temperature, saturated NaHCO$_3$ solution (30 mL) was added, and the mixture was extracted with chloroform (3×10 ml). The organic layer was dried over MgSO$_4$ and evaporated. The resulting powder was dissolved in a mixture of methanol/ethyl acetate (1:3) (10 ml). After filtering, the solution was evaporated to give the title compound (0.09 g, 10%) as a solid.

Figure 2:
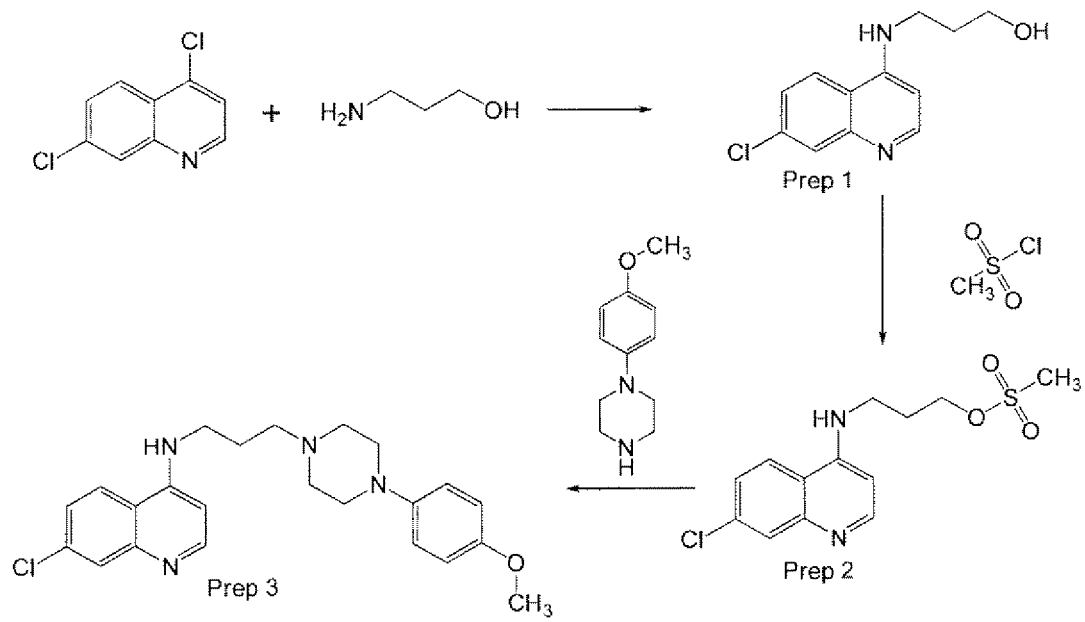
FIG. 2 shows a schematic of an exemplary synthesis protocol for 7-chloro-N-(3-(4-(4-methoxyphenyl)piperazin-1-yl)propyl)quinolin-4-amine.

FIG. 2 illustrates the exemplary synthesis as herein disclosed in Example 1.

Example 2

Assay Against CQ$^R$ and CQ$^S$ P. Falciparum Strains

This Example demonstrates that several representative compounds are highly effective inhibitors of the growth of CQ$^R$ and CQ$^S$ P. falciparum strains in vitro.

An in vitro fluorescence assay for determining IC$_{50}$ of antimalarial drugs was performed as previously described by Smilkstein et al. (2004. *Antimicrob. Agents Chemother.* 48(5): 1803-1806). This procedure can be automated for high-throughput screening of the antimalarial activities of RCQs described herein. This method also allows the tested agent (e.g., a MCQ) to be in contact with the parasite for an entire developmental cycle without purine starvation (which occurs with the commonly used $^3$H-hypoxanthine method; see, e.g., Desjardins et al. 1979. *Antimicrob. Agents Chemother.* 16, (6):710-7188).

Briefly, an initial parasitemia of approximately 0.2% was attained by addition of uninfected red blood cells to a stock culture of cells infected with Dd2 (CQ$^R$), 7G8 (CQ$^R$), or D6 (CQ$^S$) P. falciparum strains. A 10 mM solution of a test compound (in DMSO) was prepared. The test compound (at a final concentration from $10^{-11}$ to $10^{-4}$ M) and infected red blood cells (at a final concentration of 2% (v/v)) were mixed in 100 µL samples in individual wells of a 96-well plate. Each sample was prepared in triplicate. A triplicate set of reactions containing CQ (instead of the test compound) was included as a control. After a 72 hour incubation period, Sybr Green I dye-detergent mixture (100 µL) was added to each reaction. The samples were further incubated for an hour in the dark, and then placed in a 96-well fluorescence plate reader (Gemini-EM, Molecular Diagnostics) and analyzed with excitation and emission wavelength bands at 485 and 530 nm, respectively. Fluorescence readings were plotted against the Log [drug], and curve fitting performed by nonlinear regression to find the IC$_{50}$ value.

IC$_{50}$ values were calculated from these data and are summarized in the following Table 3:

TABLE 3

Assay Results of Representative Compounds for Activity Against Strains

| Compound | IC$_{50}$-D6 (nM) | IC$_{50}$-Dd2 (nM) | IC$_{50}$-7G8 (nM) |
|---|---|---|---|
| 7-chloro-N-(3-(4-phenylpiperazin-1-yl)propyl)quinolin-4-amine | <2.5 | <2.5 | |
| 7-chloro-N-(3-(4-(pyridin-2-yl)piperazin-1-yl)propyl)quinolin-4-amine | 2.7 | 4.8 | 9.5 |
| 7-chloro-N-(3-(4-(4-fluorophenyl)piperazin-1-yl)propyl)quinolin-4-amine | 0.14 | 0.8 | 0.3 |
| 7-chloro-N-(3-(4-(4-methoxyphenyl)piperazin-1-yl)propyl)quinolin-4-amine | 0.1 | 0.48 | 0.3 |

TABLE 3-continued

Assay Results of Representative Compounds for Activity Against Strains

| Compound | IC$_{50}$-D6 (nM) | IC$_{50}$-Dd2 (nM) | IC$_{50}$-7G8 (nM) |
|---|---|---|---|
| 7-chloro-N-(3-(4-(4-(trifluoromethyl)phenyl)piperazin-1-yl)propyl)quinolin-4-amine | 0.005 | 0.17 | 0.2 |
| 7-chloro-N-(3-(4-(4-chlorophenyl)piperazin-1-yl)propyl)quinolin-4-amine | 0.005 | 0.33 | 0.09 |
| 7-chloro-N-(3-(4-(3,4-dichlorophenyl)piperazin-1-yl)propyl)quinolin-4-amine | 0.1 | 0.9 | 0.28 |
| N-(3-(4-(biphenyl-4-yl)piperazin-1-yl)propyl)-7-chloroquinolin-4-amine | 0.1 | 0.36 | 0.13 |
| N-(3-(4-(biphenyl-3-yl)piperazin-1-yl)propyl)-7-chloroquinolin-4-amine | 0.94 | 1.8 | |
| N-(3-(4-(biphenyl-2-yl)piperazin-1-yl)propyl)-7-chloroquinolin-4-amine | 1.2 | 2.6 | |
| 7-chloro-N-(3-(4-p-tolylpiperazin-1-yl)propyl)quinolin-4-amine | 0.11 | 0.86 | 0.3 |
| 7-chloro-N-(3-(4-(4-nitrophenyl)piperazin-1-yl)propyl)quinolin-4-amine | 0.8 | 1.14 | 0.4 |
| 7-chloro-N-(3-(4-(pyrimidin-2-yl)piperazin-1-yl)propyl)quinolin-4-amine | 1.3 | 1.0 | 3.3 |
| N-(3-(4-(4-aminophenyl)piperazin-1-yl)propyl)-7-chloroquinolin-4-amine | 1.8 | 3.16 | 3.2 |
| 7-chloro-N-(3-(4-(2,4-dinitrophenyl)piperazin-1-yl)propyl)quinolin-4-amine | 0.3 | 0.47 | 0.35 |
| 7-chloro-N-(3-(4-(5-nitropyridin-2-yl)piperazin-1-yl)propyl)quinolin-4-amine | 0.26 | 0.48 | 0.45 |
| 7-chloro-N-(3-(4-(5-(trifluoromethyl)pyridin-2-yl)piperazin-1-yl)propyl)quinolin-4-amine | 0.5 | 0.83 | 1.0 |
| 7-chloro-N-(3-(4-(3,5-dinitropyridin-2-yl)piperazin-1-yl)propyl)quinolin-4-amine | 0.45 | 0.85 | 0.9 |
| 7-chloro-N-(2-(4-(pyridin-2-yl)piperazin-1-yl)ethyl)quinolin-4-amine | 4.57 | 3.9 | 12.23 |
| 7-chloro-N-(3-(4-(pyridin-3-yl)piperazin-1-yl)propyl)quinolin-4-amine | 2.07 | 1.1 | 2.9 |
| 7-chloro-N-(3-(4-(pyridin-4-yl)piperazin-1-yl)propyl)quinolin-4-amine | 2.07 | 2.0 | 6.8 |
| Chloroquine | 6.9 | 102 | 106 |

Example 3

Cytotoxicity Assay

MCQ cytotoxicity was determined against mitogen-induced marine spleen lymphocytes in vitro using the Alamar Blue assay (as described by Ahmed et al. 1994. *J. Immunol. Meth.* 170(2):211-224, which is incorporated herein by reference in its entirety). Mouse spleen lymphocytes were isolated from C57B1/6J mice by teasing tissues on a metallic sieve screen. Cells thus obtained were washed in RPMI 1640 media, then resuspended in complete RPMI media containing 10% FBS, 50 µg/ml penicillin/streptomycin, 50 µM β-mercaptoethanol, and 1 µM/mL concanavalin A for 1 minute. Two hundred (200) µl isolated cells were then seeded in separate wells of a 96-well flat-bottom tissue culture plate at a density of 2×10$^5$ cells per well. Test compound was added to the individual wells at concentrations of 0 to 62 µM. After 72 hours incubation in a humidified atmosphere at 37° C. and 5% $CO_2$, a solution of resazurin PBS was added to a final concentration 10 µM, and the plates were returned to the incubator for another 24 hours. Resazurin is a substrate which changes color in response to metabolic activity (such as that found in living cells). The fluorescence of the cell-containing samples was measured with a Gemini EM plate reader with excitation at 560 nM and emission at 590 nM. $LC_{50}$ values were determined from plots of florescence versus drug concentration using non-linear regression by Prism software.

The following table shows cytotoxicity values for certain test compounds.

TABLE 4

Assay Results of Representative Compounds for Cytotoxicity

| Compound | Cytotoxicity (nM) |
| --- | --- |
| 7-chloro-N-(3-(4-phenylpiperazin-1-yl)propyl)quinolin-4-amine | 6400 |
| 7-chloro-N-(3-(4-(pyridin-2-yl)piperazin-1-yl)propyl)quinolin-4-amine | 8600 |
| N-(3-(4-(biphenyl-4-yl)piperazin-1-yl)propyl)-7-chloroquinolin-4-amine | 2200 |
| N-(3-(4-(biphenyl-3-yl)piperazin-1-yl)propyl)-7-chloroquinolin-4-amine | 2100 |
| N-(3-(4-(biphenyl-2-yl)piperazin-1-yl)propyl)-7-chloroquinolin-4-amine | 1700 |
| Chloroquine | 12400 |

Example 4

In Vivo Activity

Compounds were tested in mice against *P. berghei* according to procedure disclosed here in the In Vitro and In Vivo Bioassays Section.

According to the In Vitro and In Vivo Bioassays section, male CF-1 mice at 4-5 weeks of age (about 20 g) are infected with about $10^7$ infected red blood cells via 100 µL, tail vein injection and randomly sorted into groups of 4 mice each on Day 0. One hour after infection, the mice receive the test agent via oral gavage, or by the intraperitoneal route (at approximately 1-10 times the in vitro $IC_{50}$ values). Drugs are administered once daily for at least 4 days beginning at Day 0. Animals are tested weekly for levels of parasitemia, for example, by microscopic analysis of Giemsa-stained blood smears. Efficacy of a tested compound in this bioassay is measured by inhibition of parasite growth as defined previously. In some examples, subjects are expected to be freed of measurable parasites after a period of treatment (such as 30 days).

Compounds were tested according to four variations of the procedure: single oral dose, single subcutaneous dose, first 4× oral dose experiment, and second 4× oral dose experiment. For the single oral dose, single subcutaneous dose, and the first 4× oral dose experiments, the dosage was 30 mg/kg. In the second 4× oral dose experiment, the dosage of each test drug was adjusted to an amount equimolar to 30 mg/kg CQ.

The mice were monitored for survival up to 30 days and for parasitemia, which was very low, if any. Historical CQ data is provided for comparison. For CQ, the average survival for the mice in 1) single oral dose: 9 days; 2) single subcutaneous dose: 10 days; 3) first 4× oral dose experiment: 30 days; and 4) second 4× oral dose experiment: 30 days. A negative control was run. The results for the negative control is as follows: 1) single oral dose; 4 days; 2) single subcutaneous dose: 4 days; and 3) first 4× oral dose experiment: 4 days.

7-chloro-N-(3-(4-(pyridin-2-yl)piperazin-1-yl)propyl)quinolin-4-amine was tested. The average survival for the mice tested with 7-chloro-N-(3-(4-(pyridin-2-yl)piperazin-1-yl)propyl)quinolin-4-amine in the second 4× oral dose experiment was 20 days.

Example 5

Method of Treating a Disease Caused by a *Plasmodium* Parasite

A subject presents with a symptoms of a disease that is identified as being caused by a *Plasmodium* parasite. The subject is treated with a therapeutically effective amount of a pharmaceutical composition comprising an MCQ compound as disclosed herein. The composition is administered orally at a dose of up to 200 mg/kg of body weight twice per day for a period of 3-5 days. Upon administration of the pharmaceutical composition, the subject presents with improved symptoms (e.g. abatement of fever and fatigue, improved appetite and energy) and beings to experience recovery from the disease by the end of the administration period.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be understood that the terminology used herein is for the purpose of describing particular embodiments only, and is not intended to be limiting, since the scope of the present invention will be limited only by the appended claims.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the structures that can be included or encompassed by ring 1, ring 2, $L^1$, $L^2$, $L^3$ and $L^4$. Various embodiments of the invention can specifically include or exclude any of these variations or elements.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

What is claimed is:
1. A compound having the formula:

$$Q\text{-}L^1\text{-}G \qquad (I),$$

wherein Q is:

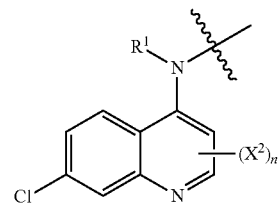

$X^2$ is an alkyl, alkoxy, amino, halogen or hydroxyl group;
n is an integer from zero to 2;
$R^1$ is hydrogen or an alkyl;
$L^1$ is a $C_{2\text{-}12}$ alkylene;
G is

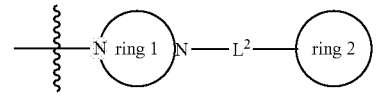

wherein
ring 1 is a 1,4-piperazinyl,
ring 2 is a cycloalkyl, phenyl, or substituted phenyl,
wherein the substituted phenyl is substituted with halo, alkoxy, alkyl, substituted alkyl, nitro, amino, cycloalkyl, phenyl, or combination thereof;

wherein the substituted alkyl is substituted with 1 to 3 halo substituents, phenyl or naphthyl; and $L^2$ is a bond or $C_{1-12}$ alkylene, or salts or stereoisomers thereof;

with the proviso:

wherein if $L^1$ is $C_2$ alkylene and $L^2$ is a bond and ring 1 is

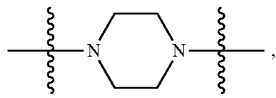 [SMILES: *N1CCN(*)CC1]

then ring 2 is not phenyl.

2. The compound of claim 1, wherein n is zero.
3. The compound of claim 1, wherein $L^1$ is $C_{2-3}$ alkylene.
4. The compound of claim 1, wherein ring 1 is 1,4-piperazinyl; $L^2$ is a bond; and ring 2 is a substituted phenyl, wherein the substituents for the phenyl are halo, alkoxy, or trifluoromethyl.
5. A method for inhibiting or treating malaria in a subject, the method comprising administering to the subject a compound of claim 1.
6. A method of preparing a compound of formula:

 (I), wherein Q is

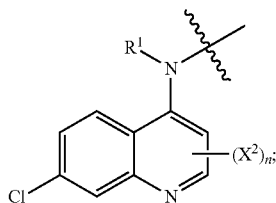

$X^2$ is an alkyl, alkoxy, amino, halogen or hydroxyl group;

n is an integer from zero to 2;

$R^1$ is hydrogen or an alkyl;

$L^1$ is $C_{2-12}$ alkylene; and

G is

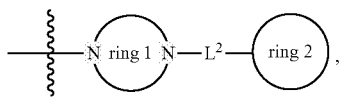

wherein ring 1 is a 1,4-piperazinyl, ring 2 is cycloalkyl, phenyl, or substituted phenyl, wherein the substituted phenyl is substituted with halo, alkoxy, alkyl, substituted alkyl, nitro, amino, cycloalkyl, phenyl, or combination thereof; and wherein the substituted alkyl is substituted with 1 to 3 halo substituents, phenyl or naphthyl; and $L^2$ is a bond or $C_{1-12}$ alkylene, or salts or stereoisomers thereof;

with the proviso:

wherein if $L^1$ is $C_2$ alkylene and $L^2$ is a bond and ring 1 is

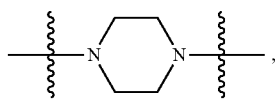 [SMILES: *N1CCN(*)CC1]

then ring 2 is not phenyl, the method comprising:

contacting a compound of formula

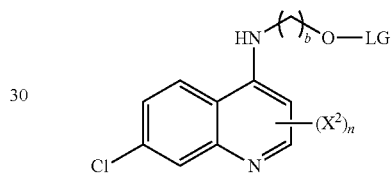

with a compound of formula

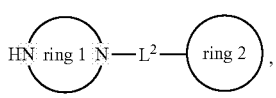

wherein O-LG represents an activated leaving group and wherein ring 1 and ring 2 are defined above.

* * * * *